(12) United States Patent
Kumar

(10) Patent No.: US 11,690,582 B2
(45) Date of Patent: Jul. 4, 2023

(54) SYSTEMS AND METHODS FOR A MOBILE MEDICAL DEVICE DRIVE PLATFORM

(71) Applicant: GE Precision Healthcare LLC, Milwaukee, WI (US)

(72) Inventor: G.S.Sampath Kumar, Hosur (IN)

(73) Assignee: GE Precision Healthcare LLC, Milwaukee, WI (US)

( * ) Notice: Subject to any disclaimer, the term of this patent is extended or adjusted under 35 U.S.C. 154(b) by 469 days.

(21) Appl. No.: 16/868,448

(22) Filed: May 6, 2020

(65) Prior Publication Data

US 2021/0345977 A1 Nov. 11, 2021

(51) Int. Cl.
*A61B 6/00* (2006.01)
*B60B 19/00* (2006.01)

(52) U.S. Cl.
CPC .......... *A61B 6/4405* (2013.01); *B60B 19/003* (2013.01); *A61B 2560/0214* (2013.01); *A61B 2560/0431* (2013.01); *A61B 2560/0437* (2013.01); *B60B 2200/26* (2013.01); *B60B 2900/531* (2013.01)

(58) Field of Classification Search
CPC .......... A61B 6/4405; A61B 2560/0437; A61B 2560/0214; A61B 2560/0431; B60B 19/003
USPC ........................................................ 348/196
See application file for complete search history.

(56) References Cited

U.S. PATENT DOCUMENTS

| | | |
|---|---|---|
| 3,876,255 A | 4/1975 | Ilon |
| 9,554,953 B2 | 1/2017 | Dirauf et al. |
| 9,751,360 B2 | 9/2017 | Rijken et al. |
| 11,389,348 B2 * | 7/2022 | Patmore ............... A61G 7/0528 |
| 2012/0128130 A1 | 5/2012 | Boomgaarden |
| 2014/0379130 A1 | 12/2014 | Lee et al. |
| 2015/0216746 A1 | 8/2015 | Dirauf et al. |
| 2016/0302986 A1 * | 10/2016 | Haladova ............... A61G 7/015 |
| 2017/0014092 A1 * | 1/2017 | Shirota ............... A61B 6/4405 |
| 2017/0325763 A1 | 11/2017 | Hoernig et al. |
| 2018/0125439 A1 | 5/2018 | Nabeta |

(Continued)

FOREIGN PATENT DOCUMENTS

| | | |
|---|---|---|
| EP | 3257463 A1 | 12/2017 |
| JP | 2012110702 A | 6/2012 |

(Continued)

OTHER PUBLICATIONS

EP application 21169756.0 filed Apr. 21, 2021—Extended Search Report dated Sep. 16, 2021; 7 pages.

(Continued)

*Primary Examiner* — Todd M Epps

(74) *Attorney, Agent, or Firm* — McCoy Russell LLP

(57) ABSTRACT

Methods and systems are provided for controlling movement of a mobile medical device drive platform. In one example, a mobile platform includes a chassis configured to house one or more medical devices, an omnidirectional wheel system including an omnidirectional wheel coupled to the chassis, a battery housed in the chassis, the battery configured to supply power to drive the omnidirectional wheel system and/or supply power to operate the one or more medical devices, and a battery charging system housed in the chassis, where the battery charging system is configured to facilitate wired and/or wireless charging of the battery.

19 Claims, 14 Drawing Sheets

(56) References Cited

U.S. PATENT DOCUMENTS

| | | | |
|---|---|---|---|
| 2018/0242932 A1 | 8/2018 | Sullivan et al. | |
| 2018/0297396 A1 | 10/2018 | Dietrich et al. | |
| 2018/0317870 A1* | 11/2018 | Fehre | A61B 6/4441 |
| 2019/0125285 A1 | 5/2019 | Nebosis | |
| 2019/0343701 A1 | 11/2019 | Dirauf et al. | |
| 2020/0315561 A1* | 10/2020 | Okumura | G01N 23/04 |

FOREIGN PATENT DOCUMENTS

| | | |
|---|---|---|
| JP | 2016120591 A | 7/2016 |
| JP | 2017023185 A | 2/2017 |
| JP | 2019146959 A | 9/2019 |
| WO | 2016165925 A1 | 10/2016 |
| WO | 2018130315 A1 | 7/2018 |

OTHER PUBLICATIONS

JP application 2021-070528 filed Apr. 19, 2021—Office Action dated Jan. 18, 2023, Machine Translation, Jan. 19, 2023; 6 pages.
JP2016120591 English Abstract, Espacenet Mar. 28, 2023; 1 page.
JP2019146959 English Abstract, Espacenet Mar. 28, 2023; 1 page.

\* cited by examiner

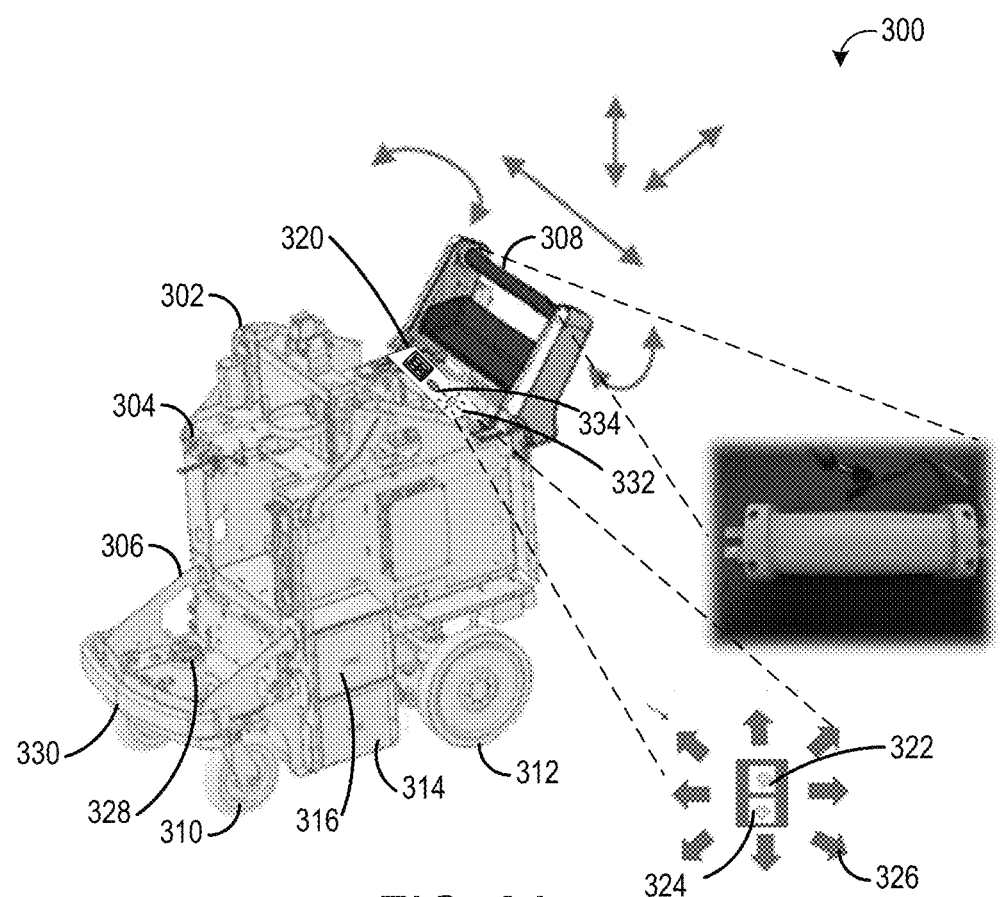
FIG. 3A
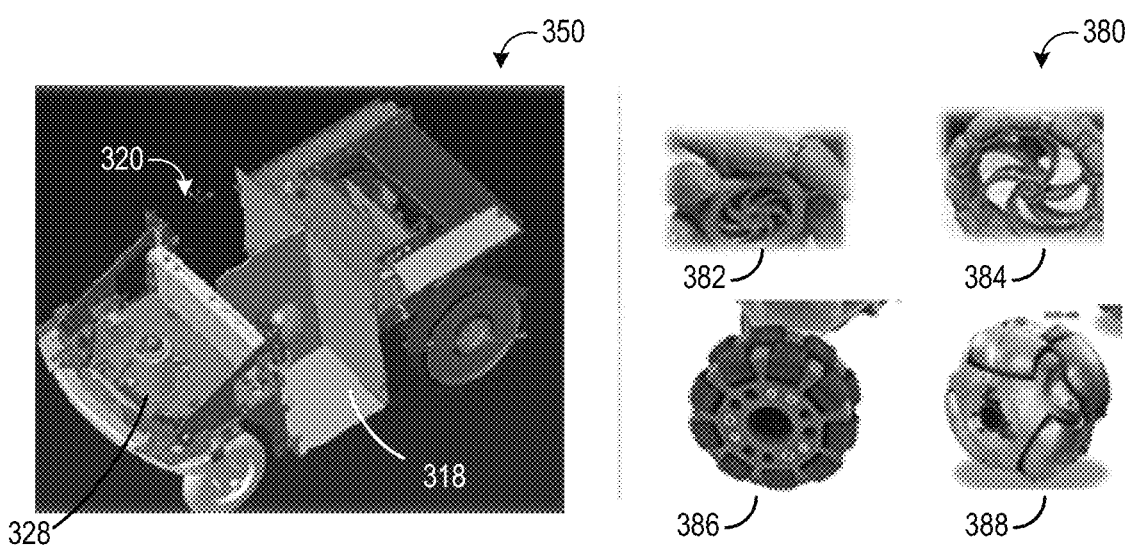
FIG. 3B
FIG. 3C

SYSTEMS AND METHODS FOR A MOBILE MEDICAL DEVICE DRIVE PLATFORM

FIELD

Embodiments of the subject matter disclosed herein relate to mobile medical device systems.

BACKGROUND

Mobile medical device systems, such as mobile x-ray devices, are often mounted on motorized carts that are driven to the patient's location. The cart typically has two main wheels in the rear that are driven to move the system. Two swivel wheels are usually provided in the front of the cart. Additionally, the medical device assembly (such as the x-ray source or tube) may be mounted on a swivel column proximate the front of the unit.

In these mobile medical device systems, the movable platform or cart has independently driven wheels that allow for some degree of steering. A drive handle may be provided at the rear of the cart, allowing the operator to push harder on one side or the other of the handle, resulting in the cart turning one direction or the other. However, some patient rooms are quite small and/or the available area in which to move the platform is limited, such as by other patient monitoring devices and machines.

BRIEF DESCRIPTION

In an embodiment, the present disclosure provides for a mobile platform, including a chassis configured to house one or more medical devices, an omnidirectional wheel system including an omnidirectional wheel coupled to the chassis, a battery housed in the chassis, the battery configured to supply power to drive the omnidirectional wheel system and/or supply power to operate the one or more medical devices, and a battery management system housed in the chassis, where the battery management system is configured to facilitate wired and/or wireless charging of the battery.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIGS. 3A, 3B, and 3C show an example mobile medical device platform.

FIGS. 3A, 3B, 3C, 5B, and 7-10 and 17 are drawn to scale, although other relative dimensions may be used if desired.

DETAILED DESCRIPTION

The present disclosure relates to a mobile platform, such as a mobile medical device platform, that includes a chassis configured to house one or more medical devices, such as an imaging system (e.g., x-ray imaging system), ultrasound, baby warmer, mobile surgery system, or anesthesia delivery system. To enable enhanced navigation in tight spaces, the chassis may include an omnidirectional wheel system, comprising an omnidirectional wheel and a corresponding wheel motor, motor drive, encoder, wheel and/or motor sensors, or other related components, coupled to the chassis. The chassis may further include a battery housed in the chassis, where the battery is configured to supply power to drive the omnidirectional wheel system and/or supply power to operate the one or more medical devices. The chassis may include a battery management system housed in the chassis, where the battery management system is configured to facilitate wired and/or wireless charging of the battery. The mobile platform may include a drive controller configured to automatically control the omnidirectional wheel system, for example to automatically to move the mobile platform to a charging station to charge the battery and/or to a requested or target location (e.g., patient room).

The drive controller may include a tangible and non-transitory computer readable medium (memory) in which programming instructions are stored. As used herein, the term tangible computer readable medium is expressly defined to include various types of computer readable storage and to exclude merely propagating signals. Additionally or alternatively, the example methods and systems may be implemented using coded instruction (e.g., computer readable instructions) stored on a non-transitory computer readable medium such as a flash memory, a read-only memory (ROM), a random-access memory (RAM), a cache, or any other storage media in which information is stored for any duration (e.g. for extended period time periods, permanently, brief instances, for temporarily buffering, and/or for caching of the information).

Memory and processors as referred to herein can be standalone or integrally constructed as part of various programmable devices (e.g., computers). Computer memory of computer readable storage mediums as referenced herein may include volatile and non-volatile or removable and non-removable media for a storage of electronic-formatted information such as computer readable program instructions or modules of computer readable program instructions, data, etc. that may be stand-alone or as part of a computing device. Examples of computer memory may include, but are not limited to RAM, ROM, EEPROM, flash memory, or any other medium which can be used to store the desired electronic format of information and which can be accessed by the processor or processors or at least a portion of a computing device.

Figure 1:
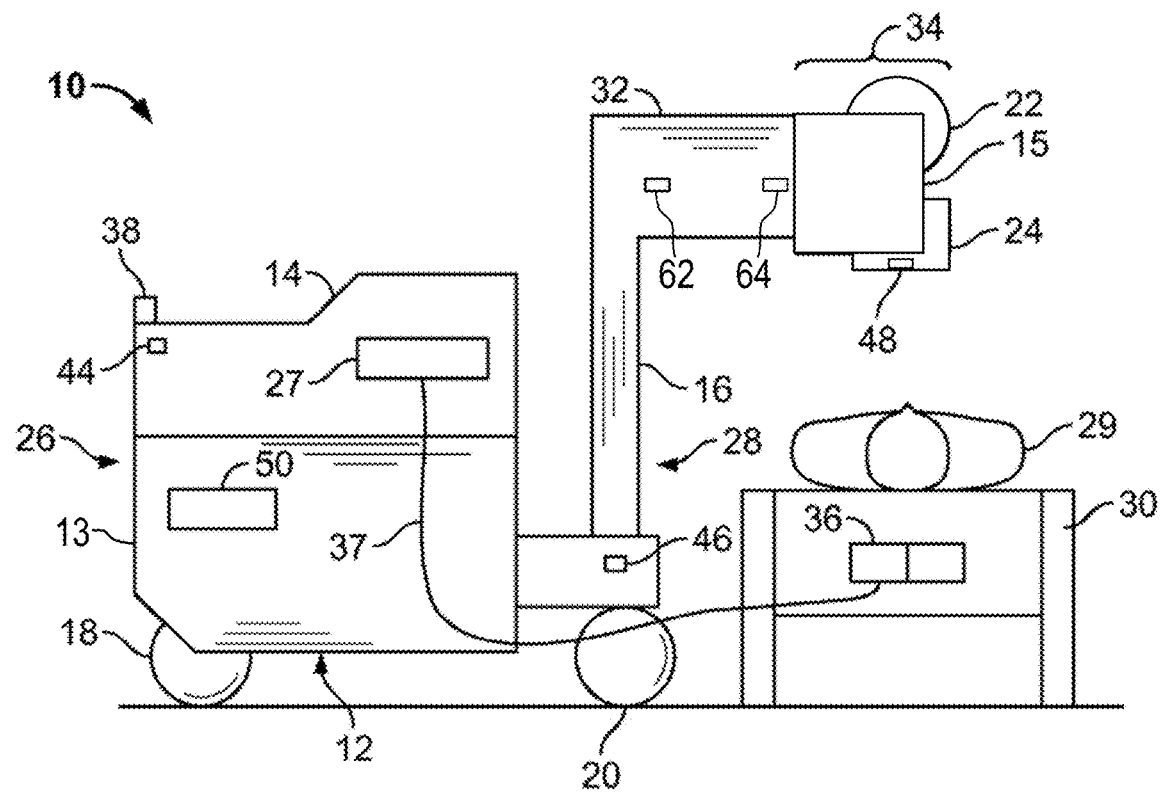
FIG. 1 is an elevation view of an example mobile imaging system.

FIG. 1 illustrates an example mobile medical device system in the form of a mobile imaging system 10 that may be used in the medical field or in other fields. The system 10 has a mobile medical device platform 12, (wheeled motorized drive assembly) and an operator console 14 that may be supported by the mobile medical device platform 12. The operator console 14 may provide a user interface for operating the mobile platform and/or for operating or communicating with and operating the medical device coupled with the mobile medical device platform 12. Mobile medical device platform 12 comprises a frame 13 (also referred to herein as a mobile chassis) and two rear drive wheels 18 (one wheel is shown) coupled to the frame at a rear end 26 of the mobile platform 12 and two front drive wheels 20 (one wheel is shown) coupled to the frame at a front end 28 of the mobile platform 12.

A column 16 or other support member is attached to, and extends upwardly from, the frame of mobile medical device platform 12 and rotates or swivels with respect to the mobile medical device platform 12. In some examples, column 16 is collapsible and thus may be comprised of multiple, nested sections that may telescope outward from the frame in response to user manipulation. A sensor 46 may detect the amount of rotation or movement of the column 16 with respect to the mobile medical device platform 12. An arm 32 is fixed to the column 16 at a predetermined rotational position. The arm 32 may be vertically adjustable relative to the frame. For example, the column may be collapsible (as described above) and the arm 32 may be moved vertically as the column is extended or collapsed. Additionally or alternatively, the arm may be configured to translate vertically along the column 16, e.g., in response to user manipulation. The arm 32 may also telescope with respect to the column 16, allowing components mounted at an outer end of the arm 32 to be moved closer to or further away from the column 16. In one embodiment, the arm 32 may have further degrees of freedom with respect to the column 16. An imaging assembly, herein in the form of a radiation source 34 including an x-ray source assembly 15, is attached to the outer end of the arm 32 and has an x-ray tube housing 22 containing an x-ray source (not shown). A collimator 24 is attached to the tube housing 22 and is rotatable with respect to the tube housing 22. A sensor 48 may be provided to detect the amount of rotation or movement of the collimator 24 with respect to the mobile medical device platform 12 and/or column 16. An x-ray detector 36 detects x-ray data and may communicate with an imaging controller 27 wirelessly or over a cable 37.

One or more sensors are positioned to detect relative movement of the arm 32, e.g., relative to the column 16. As shown, a push sensor 62 may detect movement of the arm 32 inward toward the column 16 and a pull sensor 64 may detect movement of the arm 32 outward away from the column 16. The push sensor 62 may be positioned proximate the column 16 (e.g., closer to the column than the imaging assembly) while the pull sensor 64 may be positioned proximate the imaging assembly (e.g., closer to the radiation source 34 than the column 16). However, the placement of the sensors is exemplary, and other positions are possible, such as the push sensor being positioned proximate the imaging assembly while the pull sensor is positioned proximate the column.

Push sensor 62 and pull sensor 64 may each be a mechanical switch that indicates an end of travel of the arm. In other examples, push sensor 62 and pull sensor 64 may be optical sensors, magnetic sensors, pressure/force sensors, inertial measurement units (IMUs), or any variation of these sensors. If the sensors are potentiometers or encoders, the degree of extension of the arm may be measured continuously, with end of travel positions defined by predefined values within the extension range. It should be noted that the sensors of the various embodiments may be a suitable type or types of sensors. For example, one or more of the sensors may operate based on sensing a change in distance using optical, magnetic, electrical, or other mechanisms.

A first hand-actuatable interface is provided on mobile platform 12, herein in the form of a drive handle 38 provided on the rear end 26 of the mobile platform 12, such as coupled to the frame of mobile medical device platform 12. A drive controller 50 senses or receives signals based on the manipulation (e.g., user manipulation) of the drive handle 38, and thus the mobile platform 12 may be driven to different locations to image a subject 29 based on multi-directional sensing via the force sensors. The mobile medical device platform 12 may have at least one motor (shown in FIG. 2) and is capable of driving the rear drive wheels 18 and the front drive wheels 20 separately.

The subject 29 is typically lying on a bed or table 30. Once the mobile platform 12 is positioned near the table 30, the column 16 is swiveled or rotated (e.g., via user manipulation) to position the x-ray source assembly 15 over the subject 29. The x-ray detector 36 is positioned on the opposite side of the subject 29.

A user interface 44 may be provided proximate the rear end 26 of the mobile platform 12. Optionally, the user interface 44 may be integrated with the drive handle 38 or the operator console 14, or it may be configured as a remote control that may be held in the operator's hand away from the mobile platform 12. The user interface 44 may communicate with the drive controller 50 wirelessly or over a wired connection. The user interface 44 may be one of, or a combination of, a button, joystick, toggle switch, power assist handle, provided as a key on a keyboard or a selection on a touch screen, and the like.

In some examples, the user interface 44 may be in the form of the drive handle 38. In such an example, manipulation of the drive handle 38 may result in signals being sent to the drive controller 50 to control movement of the mobile platform 12. In some examples, the signals sent by the drive handle 38 may be different than the signals sent by the user interface 44. For example, the user interface 44 may send signals to switch drive modes, power on or off the mobile platform 12, etc., while the drive handle 38 may send directional and force signals to instruct the drive controller 50 how to power the wheels. Example methods for how the drive handle 38 and/or user interface 44 are used to drive the vehicle are shown and described in more detail in FIGS. 12 and 15.

The drive controller 50 receives angle information from the sensor 46 and the sensor 48 that indicates the position of the column 16, arm 32, collimator 24, and/or x-ray source assembly 15. Further, drive controller 50 receives arm movement information from sensors 62 and 64 that indicates the extension/movement of the arm (and the associated movement of the imaging assembly coupled to the arm). When the operator moves the imaging assembly and/or arm to an end-of-travel position (e.g., where telescoping motion of the arm stops and further movement of the arm is transmitted to the column), the mobile platform 12 may be moved based on, for example, the angle of rotation of the column 16 with respect to the mobile medical device platform 12 and the direction of movement of the arm. In another embodiment, the collimator 24 may be rotated or adjusted with respect to the x-ray tube housing 22. Therefore, the angle relationship between the collimator 24 and the mobile medical device platform 12 will also change. The drive controller 50 may then move the mobile platform 12 (e.g., engage motor(s) within the mobile medical device platform 12 to cause the rear drive wheels 18 and/or front drive wheels 20 to move and/or rotate the column 16) based on the angle of rotation of the collimator 24 with respect to the mobile medical device platform 12. It should be understood that different angles of rotation with respect to the mobile medical device platform 12 may be used. Further, the drive controller 50 may be configured to automatically drive the wheels in order to operate the mobile platform 12 in a self-navigate mode where the system is automatically moved to a wired and/or wireless charging station and/or other target location.

Thus, via user interface 44, an operator may raise and lower a collapsible column and/or extend and/or rotate portions of an arm mounted on a fixed or collapsible column on which a medical device has been installed. Further, via user interface 44, an operator may send instructions to a communicatively coupled medical device installed on the platform in order to coordinate the movement of the platform, column, or arm with device settings. For example, in order to position a patient within the reference frame of an x-ray device mounted on a platform, an operator may move the wheels of the mobile platform forward, rotate column 16, extend arm 32, and adjust the settings of collimator 24, all via user interface 44. How the platform and its components may be moved, rotated, and positioned is described in more detail in FIGS. 11-15.

Figure 2:
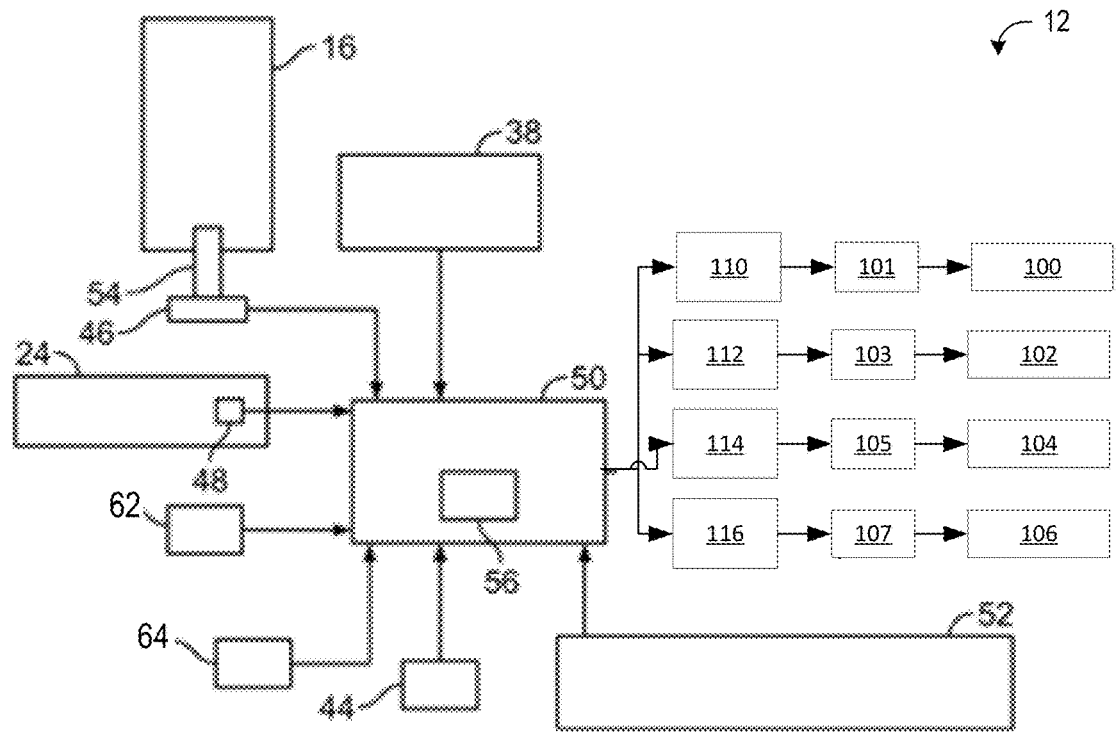
FIG. 2 is a block diagram of the components for rotation-based driving of the system of FIG. 1.

FIG. 2 is a block diagram of the components for driving the mobile medical device platform 12 of FIG. 1. As discussed previously, when moving to another room and during initial positioning, the drive controller 50 receives drive input(s) from the drive handle 38 (and/or user interface 44) from multi-directional sensing via the force sensors. Based on the drive input(s), the drive controller 50 outputs velocity information to the motor drives 110, 112, 114, and 116, to drive one or more of first drive wheel 100, second drive wheel 102 (which in one embodiment are the rear drive wheels 18 shown in FIG. 1), third drive wheel 104, and fourth drive wheel 106 (which in one embodiment are the front drive wheels 20 shown in FIG. 1) via first motor 101, second motor 103, third motor 105, and fourth motor 107, respectively. In some examples, each of first drive wheel 100, second drive wheel 102, third drive wheel 104, and fourth drive wheel 106 may be omni wheels including rollers positioned around the circumference of the wheel.

Further, in some examples, additionally or alternatively, each of first drive wheel 100, second drive wheel 102, third drive wheel 104, and fourth drive wheel 106 may be Mecanum or omni or multidirectional wheels. At any time during operation, the drive controller 50 may be configured to receive and act upon an input from one or more emergency stop mechanisms 52, which may include one or more of a button, sensor, bumper and the like.

In one embodiment, the bottom of the column 16 is connected to a shaft 54 that extends from the mobile medical device platform 12. The sensor 46 is connected to the shaft 54 to detect the rotation of the column 16. The sensor 46 provides the rotation information to the drive controller 50. The sensor 46 may be an optical sensor, magnetic sensor, Hall effect sensor, or other suitable sensor adapted to detect the degree of rotation of column 16. It should be understood that other encoder or sensor configurations may be used to sense the rotation of the column 16. The sensor 48 mounted to or proximate the collimator 24 senses rotation of the collimator 24 and provides the rotation information to the drive controller 50. Push sensor 62 and pull sensor 64 are located on or within arm 32 and sense movement of the arm (and associated imaging assembly), and provide arm extension/movement information to the drive controller 50. In one example, push sensor 62 may provide output to the drive controller 50 that the drive controller 50 may use to determine if the arm has reached a first end-of-travel position. Pull sensor 64 may provide output to the drive controller 50 that the drive controller 50 may use to determine if the arm has reached a second end-of-travel position. The sensor 46, the sensor 48, the push sensor 62, and the pull sensor 64 may communicate with the drive controller 50 wirelessly or over wired connections.

When the drive controller 50 receives input from push sensor 62 and/or pull sensor 64, a rotation-based drive module 56 of drive controller 50 may determine the velocities for each of the drive wheels based on the rotation information provided by one or both of the sensors 46 and 48, as well as the particular input from the sensors 62 and 64 indicating a direction of movement of the arm/radiation source (e.g., toward or away from the operator).

Mobile medical device platforms, such as the mobile platform 12 described above, may be used in a variety of medical settings. These medical settings may include patient bedside environments, where an operator of a mobile medical device platform may desire to move the mobile platform from a home/parking or other position to the patient bedside. Further, in some examples, mobile medical device platforms may be moved throughout a medical facility, such as from one patient/exam room to another. Properly positioning and/or navigating the mobile medical device platform in tight spaces, such as at the patient bedside, while avoiding collision with objects in the environment may be challenging. Further, such mobile medical device platforms may include batteries that may be recharged regularly. Traditional wired charging mechanisms including a charging cable may be prone to degradation (e.g., cable degradation and/or cable spooling issues). The operator attention and time taken to carefully navigate the mobile medical device platform to the various locations where imaging is to occur, as well as navigate the mobile medical device platform to a home position for battery charging and ensure battery charging occurs without undue stress on the charging cable, may result in operator/clinician resources being stretched thin, increase the cognitive load on care providers, and/or cause premature degradation of the mobile medical device platform.

Thus, according to embodiments disclosed herein, a mobile medical device platform (e.g., mobile medical device platform 12 of system 10 of FIGS. 1 and 2) may include a mobile chassis on which medical device components (e.g., radiation source, x-ray detectors, etc.) may be mounted. The mobile chassis may include highly maneuverable wheels (e.g., the omnidirectional wheels described above with respect to FIGS. 1 and 2) and a hybrid user interface via which an operator may move the mobile medical device platform, thereby providing the mobile medical device platform with the ability to turn in any direction (e.g., at any angle out of 360° possible degrees of rotation), supporting flexible position change and aiding in navigating along the shortest path to a destination. Further, position sensors (such as optical sensors) may be positioned along a surface (e.g., a forward-facing surface) of the mobile chassis. The position sensors may detect objects in the path of the mobile medical device platform and, when objects are detected, the mobile medical device platform may be slowed or stopped to avoid collision.

The mobile chassis may further include one or more batteries configured to supply power to the motors driving the wheels as well as supply power for operating the components of the mobile medical device platform. The charging/discharging of the batteries may be controlled by a battery management system also included in the mobile chassis. The battery management system may execute a charging/discharging algorithm for the batteries, may convert the AC of the charger to DC for supplying to charge the battery, and/or may monitor battery performance (e.g., voltage, current, temperature).

The batteries may be recharged via wired and/or wireless charging. In some examples, the mobile chassis may include a non-cabled wired charging docking mechanism that may be positioned at a charging station in order to charge the batteries. In some examples, the mobile chassis may be configured to self-navigate to a charging station using a search sensor (e.g., LiDAR, optical, infrared). The charging station may be configured with a trigger sensor that may be used to detect when the mobile chassis/mobile imaging system has been positioned at the charging station, so that charging may commence. To initiate the self-navigating to the charging station, a user may enter an input to the mobile medical device platform, such as an input to a user interface of the mobile medical device platform. In this way, via a simple user input to the mobile medical device platform, the mobile medical device platform may self-navigate to a charging station, dock with the charging station, and be charged, without additional user action. FIGS. 5A, 5B, 6A, and 6B illustrate in more detail how the mobile medical device platform may dock with a charging station.

The mobile chassis may be configured as a platform for moving and supplying power to an imaging system, such as the x-ray system described above. However, the mobile chassis may be used to move and supply power to other imaging systems, such as ultrasound systems, or used to move/power non-imaging systems, such as anesthesia systems.

FIG. 3A shows an example mobile platform 300 that may be used in the systems of FIGS. 1-2, including a medical device platform 302 mounted on a mobile chassis 306. The mobile platform 300 further includes a drive handle 308 (e.g., drive handle 38 of mobile medical device platform 12 in FIG. 1), two front wheels (including front wheel 310), and two rear wheels (including rear wheel 312). The mobile chassis 306 includes a battery 316 and a battery management system 314. While FIG. 3A shows one battery and corresponding battery management system, it is to be appreciated that the mobile chassis 306 may include additional batteries and/or battery management systems, such as another battery and corresponding battery management system on the opposite side of the mobile chassis.

Mobile platform 300 includes a hybrid user interface (UIF) drive handle 308 (e.g., drive handle 38 shown in FIG. 1) for operating e.g., driving) the mobile platform. The hybrid user interface drive handle is capable of sensing direction with 360 degrees of freedom in the ground plane, sensing the expected (operated) motion direction as a vector and providing input to the motion control system. As discussed earlier, handle 308 may include two or more force-sensing handle regions (e.g., pressure sensors) which may be located on each side of the handle, for interpreting user input in the form of differences in pressure or movement of the right and left sides of the handle. For example, mobile platform 300 may interpret user input in the form of forward pressure to both sides of the handle (e.g., pushing) as instructing the mobile platform to power the wheels in order to generate forward movement. Alternatively, mobile platform 300 may interpret forward pressure on one side of the handle and backward pressure on the other side of the handle as instructing the mobile platform to rotate in place, or it may interpret lateral pressure to the handle as instructing the mobile platform to move in a lateral direction. The sensors may be magnetic sensors, optical sensors, force transducer arrangements, inertial measurement units (IMUs), or any variation of these sensors that supports movement linearly in X,Y space with 360 degree rotation. Example illustrations of how pressure on the drive handle may be translated into wheel movements are shown below in FIG. 15. In one example, the handle may include two handle regions (e.g., on the left and right sides of a common handle bar), each with its own multi-directional force sensor. In an example configuration, each multi-directional force sensor can sense forces that are forward/backward, as well as a magnitude of a force vector in that direction. Thus, if a left force vector for a user is forward at a 45-degree angle downward and a right force vector from the user is forward at a 45-degree angle, each sensor senses the forward component of that force vector, respectively. Then, the wheel motors can be adjusted to provide velocities that are proportional to the sensed force vectors. In an example, the left and right sensed force vectors in the forward/rearward direction are added together form a direction vector magnitude and angle direction to control wheel commands and provide a desire velocity proportional to the sensed combined force and in a direction of the combined force vector. As illustrated further with regard to FIG. 15, the sensed magnitude of the left/right force vectors can be combined to form a turning direction proportional to a difference in the left/right force vectors, for example. In an example, a proportionate determination can be based on a gain multiplied by the parameter, which may be a linear gain or may be a gain that is a function of parameters such as weight of the mobile platform, for example.

Mobile platform 300 may also have a user interface 320 (e.g., user interface 44 of mobile imaging system 10 in FIG. 1) as part of an operator console such as operator console 14 of mobile imaging system 10 in FIG. 1, which may include alternative interfaces for operating or driving the mobile platform, such as a touch display, joystick or similar control device located on the back side of the mobile platform near the drive handle. In an embodiment, user interface 320 may comprise a touch screen 332 with one or more selectable elements (e.g., buttons) which when selected instruct the mobile platform to move in a given direction or rotate in place. For example, touch screen 332 may include rotate buttons 322 and 324 for instructing the mobile platform to rotate in place counterclockwise or clockwise, respectively. Rotate buttons 322 and 324 may be surrounded by directional movement buttons 326, indicated by arrows which when selected instruct the mobile platform to move in a forward, backward, lateral, or diagonal direction, such that an operator can direct the mobile platform to a location by sequentially selecting the relevant buttons. In some embodiments, the mobile platform may support the selection of the plurality of directional buttons at the same time in order to more precisely define how the mobile platform may be moved. For example, an operator may select two adjacent directional arrows simultaneously in order to instruct the mobile platform to move in a direction that represents the sum of their vectors.

Alternatively, user interface 320 may comprise a joystick that similarly allows an operator to instruct the mobile platform to move linearly in any direction (e.g., 360 degrees). In some embodiments, a joystick may operate based on haptic or force feedback sensors such that the pressure applied to the joystick indicates a desired speed or acceleration of the mobile platform. In other embodiments, a joystick may operate based on magnetic sensors (e.g., Hall effect sensors) or any other type of sensor that supports movement linearly in X,Y space with 360 degree rotation. Alternative driving mechanisms such as a touch screen or joystick are mentioned for illustrative and non-limiting purposes, where another similar functional user interface may be substituted. Further, other types of informational displays or navigational controls may be incorporated into graphical user interface 320 of mobile platform 300. For example, a floorplan or similar two-dimensional layout may be displayed, within which the location of mobile platform 300 may be depicted. In other embodiments, video displays may be incorporated into graphical user interface 320. For example, when operating a mobile platform where the medical device being transported is so large that the driver is prevented from seeing over or around it, one or more video cameras 304 located on the front sides of the mobile platform may display real-time video images to the driver via graphical user interface 320 showing the path of the mobile device and any obstacles in its way.

Alternatively or additionally, mobile platform 300 may include one or more collision detection sensors 330 mounted on the front of mobile platform 300, which may automatically halt the platform if it collides with an object in its path. In an embodiment, the collision detection sensors may be pressure sensors located on a bumper that extends horizontally and/or vertically across the front of the mobile medical device platform, which is activated when the platform touches or is impacted by an object in its path. The collision detection sensors may also include ultrasound or similar proximity sensors, or any other type of sensor capable of being triggered upon a collision or proximity within a given threshold (for example, a threshold distance of 6 inches from the front of the mobile platform), as described in further detail with respect to FIGS. 4A and 4B. Mobile platform 300 may also include an emergency stop button 334 in user interface 320 or similar control for immediately halting the mobile platform in place, to avoid an obstacle or similar imminent risk.

Mobile platform 300 may include omnidirectional rear drive wheels 312, such as drive wheels 100 and 102 of FIG. 1. The omnidirectional drive wheels may be Mecanum (e.g., double cone) wheels or another kind of omni-wheel, as described below with respect to FIG. 3C. Mobile platform 300 may include additional omnidirectional drive wheels 310 at the front of the mobile platform for increased power, responsiveness, or ease of movement. Other embodiments may include non-powered wheels at the front of the mobile platform (e.g., casters).

The mobile platform 300 may include an adjustable column base 328 at the front of the mobile medical device platform, upon which a column such as column 16 of mobile device mobile platform 12 in FIG. 1A may be installed for mounting elements of the medical device being transported by the mobile platform. For example, an x-ray device being transported by mobile platform 300 may include a C-arm on the front supported by a column installed on column base 328, such that mobile platform 300 can wheel the x-ray device directly up to the patient.

FIG. 3B shows a 3-D rendering 350 of one example of the mobile chassis 306 of FIG. 3A with the medical device frame removed. Mobile chassis 306 may include modular compartments 318 and 320 for housing the batteries and battery management system on either or both sides of the mobile medical device platform such that the batteries and battery management system may be easily removed (e.g., to be replaced when degraded) and for flexibility in use. For example, in some environments the mobile medical device platform may be parked and/or charged in a position in which either compartment 318 or 320 may be blocked and visual verification or replacement of a battery or the battery management system may not be possible. Alternatively, center of gravity considerations may favor the weighting of one side or the other. For example, if a device installed on the platform extends laterally out over one side of the mobile platform, the battery or batteries and battery management system may be positioned on the opposite side of the mobile platform to offset the weight.

As shown in FIG. 3B, compartments 318 and 320 may be located at the center of the mobile medical device platform, between the front and rear wheels, and at the bottom of mobile chassis 306. Low, central positioning may be advantageous in order to facilitate wireless charging over a floor-mounted charging station, to provide stability while maneuvering, and/or to lower the overall height of the platform for more efficient access to the medical device installed upon the mobile medical device platform. Further, a centralized, compact battery stacking arrangement may reduce the footprint of the mobile medical device platform, allowing for more efficient storage and maneuverability.

In other embodiments, a more efficient arrangement of mobile medical device platform components may be obtained by using a skateboard chassis, as described later, comprising a flat platform upon which components may be flexibly installed according to customized needs.

Mobile platform 300 may include omnidirectional wheels for flexible, easy driving maneuverability, as omnidirectional wheels can power the mobile platform in any direction (i.e., 360-degree mobility) with no minimum wheel radius. FIG. 3C shows an example selection 380 of omnidirectional wheels, including a Mecanum (e.g., double cone) wheel 382 and example omni-wheels 384, 386, and 388 in an assortment of wheel configurations. It should be appreciated that FIG. 3C is for illustrative purposes only and shall not be construed as limiting with respect to type, wheel configuration, number or shape of rollers, or other relevant characteristic.

Figure 4A:
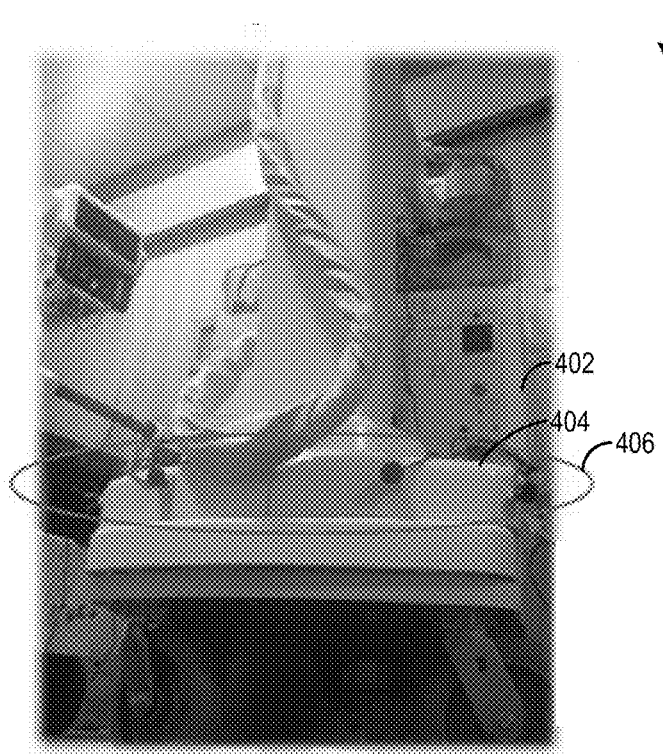
FIGS. 4A and 4B show example proximity sensors mounted on a mobile medical device platform.
Figure 4B:
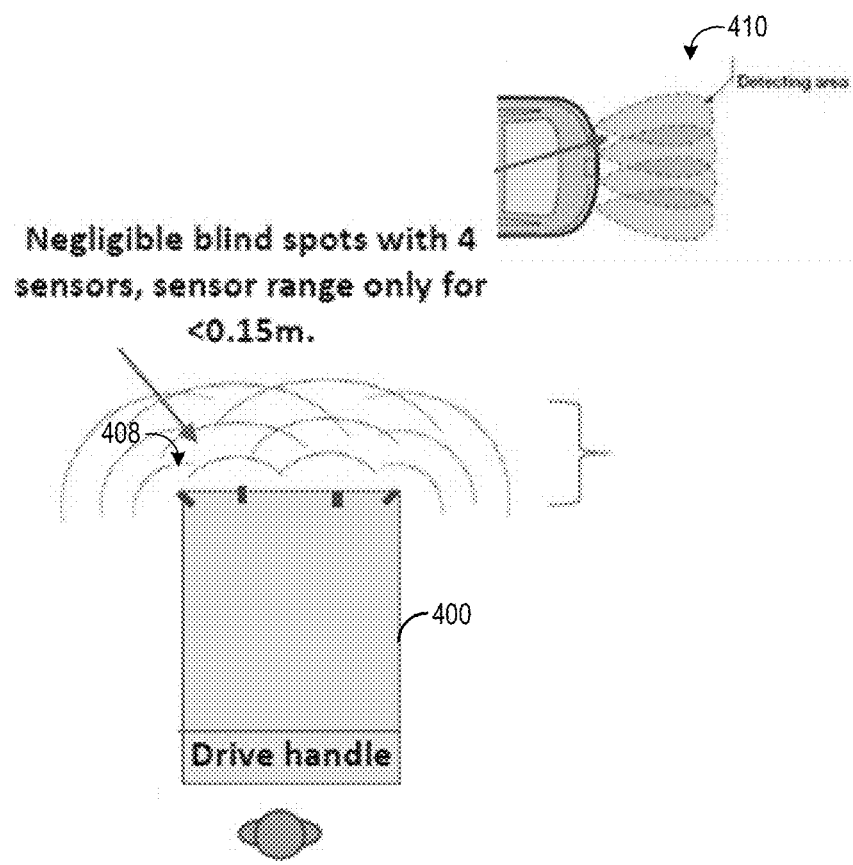

To assist in collision avoidance, the mobile chassis described herein may include a plurality of proximity sensors positioned on a front-facing surface of the mobile chassis, as described above with respect to collision detection sensor 330 of mobile platform 300. FIGS. 4A and 4B illustrate example proximity sensors that may be mounted on the mobile chassis. FIG. 4A shows an example mobile medical device platform 400 including a medical device housing 402 (housing medical device components) coupled to a mobile chassis 404 such as frame 13 of FIG. 1. One or more video cameras such as video cameras 304 of mobile platform 300 may be mounted on mobile chassis 404 in order to aid in manual or automatic navigation, as described above with respect to mobile platform 300. Two proximity sensors are mounted on the mobile chassis 404, as indicated generally by the circled region 406.

FIG. 4B schematically shows the mobile medical device platform 400 from a top-down view with a plurality of proximity sensors 408 arranged on a front-facing surface of the mobile medical device platform/mobile chassis. The front-facing surface may be the surface most likely to face forward when the mobile medical device platform is being moved by a user, and thus may be on an opposite side of the mobile medical device platform from the drive handle. As shown schematically at 410, four proximity sensors may be spaced along the front-facing surface of the mobile chassis, thereby providing overlapping detecting areas and few or no blind spots. The proximity sensors may be mounted over the front cover of the mobile chassis. The proximity sensors may be optical sensors (e.g., cameras, LiDAR, Laser sensors), which provide longer distance sensing than other sensors. However, in some examples, the proximity sensors may be bumper sensors, ultrasonic sensors, or other suitable proximity sensors.

The proximity sensors may work in conjunction with the drive controller or other elements of the mobile platform to facilitate navigability and ease-of-use with respect to operation and parking in tight quarters. Feedback from the proximity sensors may be used to control the speed of the mobile medical device platform. For example, if the signals output from the proximity sensors indicate that an object is present in the path of the mobile medical device platform within a threshold range of distance (e.g., if the object is 1-2 m away from the mobile imaging platform), the speed of the mobile medical device platform may be automatically reduced (e.g., to half the current driving speed). If the signals output from the proximity sensors indicate that an object is present in the path of the mobile medical device platform within a second threshold range of distance (e.g., less than 1 m), the mobile medical device platform may be automatically stopped. Further, proximity sensors may function in conjunction with other types of sensors mounted on the mobile medical device platform in order to dynamically adjust the mobile medical device platform's speed based on the size, weight, or extension of a mobile device over the footprint of the mobile medical device platform. For example, when the mobile medical device platform has a C-arm installed on it that extends beyond the edge of the platform, thus affecting its center of gravity, the system may adjust motion control parameters in navigating. For example, the drive controller may combine this information with proximity sensor information to determine limits to be imposed on the speed, acceleration, and/or turning radius for navigating to the desired location. Methods for how acceleration and rotation limits may be calculated and used to moderate user input are described in more detail with respect to FIGS. 12 and 13.

Thus, the drive handle, drive controller, proximity sensors, battery management sensors, device configuration sensors such as sensor 46, push sensor 62, and pull sensor 64 of mobile medical device platform 12 in FIGS. 1 and 2, and other sensors may function together as an integrated system in order to optimize movement for ease-of-use, travel time, or other factors.

Figure 5A:
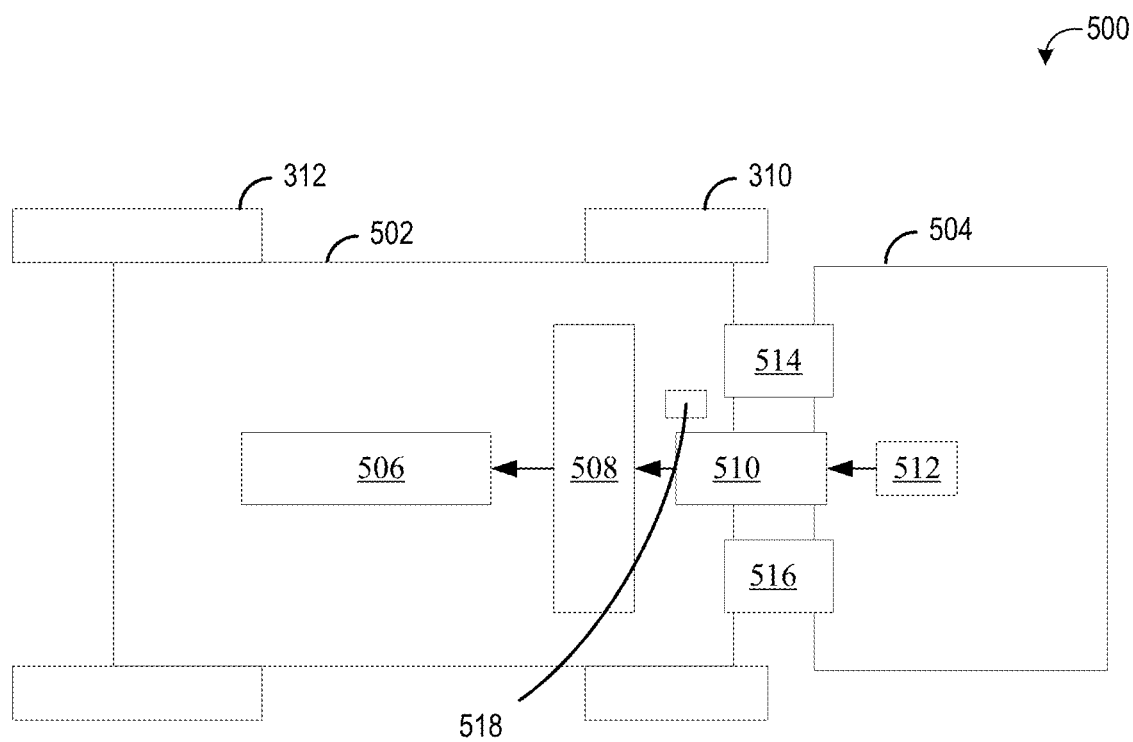
FIGS. 5A and 5B show an example wired charging system for a mobile medical device platform.

The mobile chassis described herein may be configured for wired and/or wireless charging of batteries with self-navigation capabilities to a charging station. FIG. 5A schematically shows an example wired charging system 500 for a mobile chassis such as frame 13 of mobile platform 12 in FIG. 1. As shown in FIG. 5A, a mobile chassis 502 (e.g., configured to support an x-ray imaging system) includes a battery 506, a battery management system 508, one or more docking mechanisms 514 and 516, and a charging port/component 510. In some embodiments, charging port/component 510 may be located within or as part of docking mechanisms 514 and 516. In other embodiments, charging/component 510 may be housed outside of docking mechanisms 514 and 516, as shown in FIG. 5A. Via the docking mechanisms, the charging port of the mobile chassis may be brought into contact/position with a charging station 504 for wired charging of the battery of the mobile chassis. The charging station 504 may initiate wired charging of the battery 506 via a sensor 512 located on the front of the charging station 504 that indicates when the mobile chassis is in position and electronically connected to the charging station 504. Sensor 512 may be an optical sensor (e.g., camera, LiDAR, laser sensor), infrared sensor, bumper sensor, ultrasonic sensor, or other suitable sensor. In FIG. 5A, the battery 506 and battery management system 508 are shown in the center of the mobile medical device platform; it should be appreciated that other embodiments may house these components on one side of the platform or the other for weight, center of gravity, access, or other considerations, as discussed earlier.

The mobile medical device platform may include one or more additional docking sensors 518 located on the front of the mobile medical device platform specifically to aid the drive controller in auto-navigating to the charging station or an automatic docking procedure. An automatic docking sensor 518 may also work in conjunction with the docking mechanism, proximity sensors, drive handle, column, arm, or device sensors such as sensors 46 and 48, or other sensors to optimize functioning in order to achieve a smooth approach to the charging station, secure docking, and initiation of charging. The docking sensor 518 may be a vision sensor, LiDAR, infrared sensor, or any other suitable type of vision sensor.

Battery 506 may be a lithium ion battery (e.g., about 12 AH to 15 AH), lead acid battery (about 20 AH), lead crystal battery (about 20 AH), or any functionally similar kind of battery designed in the future. The battery management system may include a rectifier or other components to adjust the alternating current of the power supply (e.g., from the grid via the medical facility) to direct current to be supplied to charge the battery. The battery management system may further include sensors/algorithms for monitoring the voltage, current, and temperature of the battery to assess the health, state of charge, etc., of the battery. The charging station may be configured to supply 230V or 120V AC. The battery management sensors may be connected to the drive controller, such that voltage, current, temperature, or other data may be used as inputs to an algorithm for powering the wheels to move the mobile platform. For example, the maximum speed of the mobile medical device platform may be reduced in order to conserve charge in the battery if the battery state of charge is low, such as 30% charged or lower. The battery management system 508 may also include a charging/discharging algorithm for charging the battery. For example, a selection of charging options may be available at a wired charging station depending on the type, size, or configuration of a battery installed on the mobile platform. The battery management system may determine and select which charging option is most appropriate for a given mobile platform setup by applying pre-established rules, and/or monitor the current entering the battery and cell voltages to determine when the battery has been sufficiently charged.

As mentioned above, the battery and battery management components may be modular units that can be removed, replaced, or exchanged for new or different models in the future in order to facilitate customization. Thus, the mobile medical device platform provides a universal chassis design that may accommodate various battery configurations and arrangements based on evolving needs and a growing and diverse set of portable medical devices being transported.

Figure 5B:
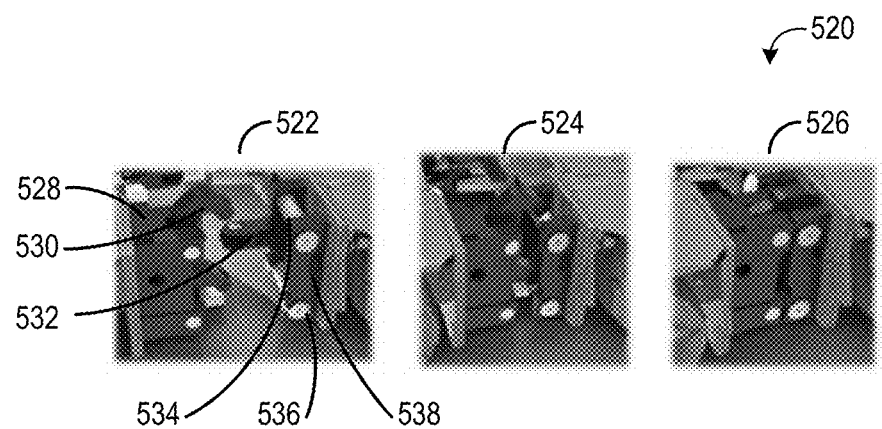

In FIG. 5B, an example series of images 520 shows a process for docking the mobile chassis via docking mechanisms 514 and 516. As shown in first image 522, the docking mechanism 516 of the mobile chassis may include a housing surrounding a charging port (not visible in the first image 522), a top hook 530, and/or a bottom hook (not visible in the first image 522). The mobile chassis may be moved (whether automatically in a self-navigation mode or under control of an operator) to align a docking mechanism housing 528 with a complimentary docking housing 538 on a charging station.

The complimentary docking housing 538 on the charging station may include a protruding docking guide 532 that slides into a similarly sized aperture on the mobile chassis (not visible in first image 522) to ensure proper alignment of the mobile chassis docking housing and the charging station docking housing. Complimentary docking housing 538 may include a top docking bar 534 and a bottom docking bar 536 for securing the mobile chassis to the charging station. As shown in second image 524, the top hook 530 may be secured over top docking bar 534 of the complimentary docking housing 538 of the charging station such that the top hook acts to maintain the mobile chassis in secure attachment with the charging station, as shown in third image 526. Additionally or alternatively, a bottom hook may be secured under bottom docking bar 536 such that the bottom hook acts to maintain the mobile chassis in secure attachment with the charging station (not shown in the set of images 520). Once charging has finished and the mobile chassis is moved out of the charging position, the top hook 530 may be actuated upward to release the top hook 530 from the top docking bar 534, or the bottom docking hook may be actuated downward to release the bottom docking hook from the bottom docking bar 536, and the mobile chassis may be moved away from the charging station.

It should be appreciated that the top (or bottom) hook or hooks are shown for illustrative purposes only and may not be considered limiting. Other embodiments of docking mechanisms 514 and 516 may include alternative mechanisms for securing the mobile platform to the charging station. The docking mechanism may also work in conjunction with the drive handle, drive controller, proximity sensors, battery management sensors, and other sensors as an integrated system in order to facilitate automatic docking, in the case in which the mobile medical device platform auto-navigates to the charging station. In other embodiments, in situations in which the mobile medical device platform is not auto-navigating to the charging station but is being operated manually, the drive controller may work in coordination with the docking mechanism, proximity sensors, drive handle, sensors for determining device configuration, and other similar components to assist the user in docking the platform to the charging station. For example, as a user manually navigates the mobile platform to the charging station, when the proximity sensors indicate that the mobile platform is in close proximity to the docking housing of the charging station, the drive controller may supersede manual control of the drive handle navigate itself to the charging station via the sensors.

Figure 6A:
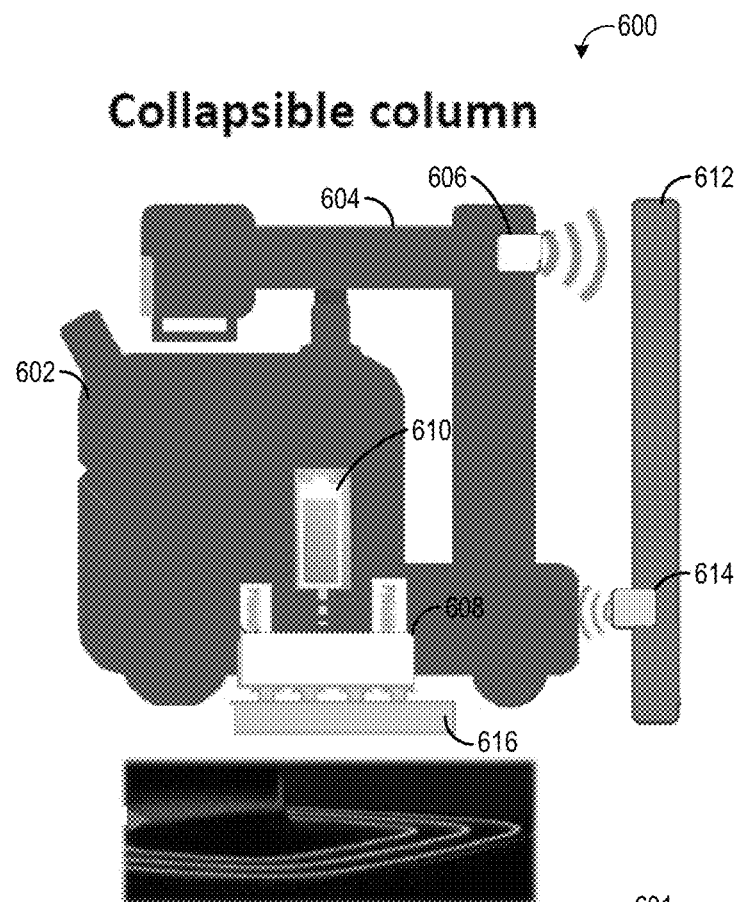
FIGS. 6A and 6B show example wireless charging systems for a mobile medical device platform.
Figure 6B:
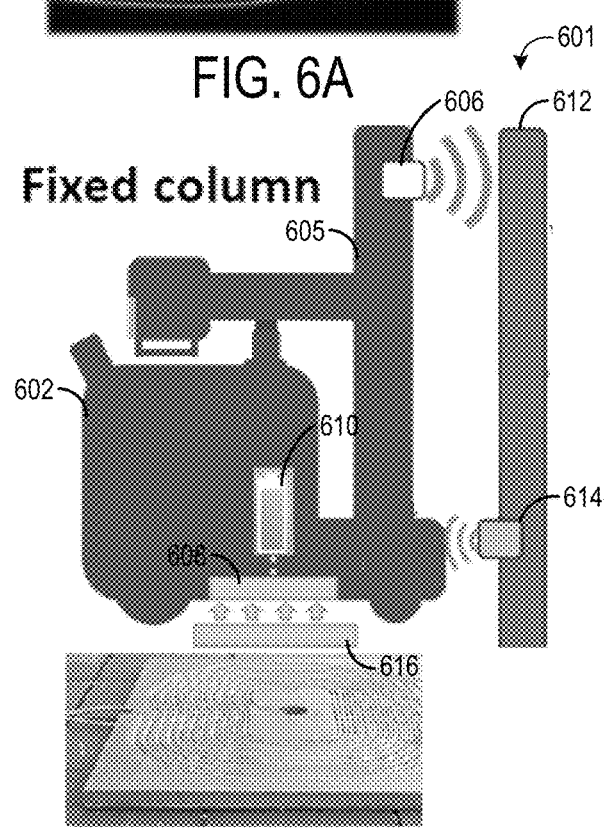

As an alternative to wired charging via a docking mechanism, FIGS. 6A and 6B schematically show example wireless charging and navigation systems for a mobile chassis such as frame 13 of mobile platform 12 in FIG. 1. As shown in FIG. 6A, a first example 600 of a wireless charging and navigation system includes a mobile medical device platform 602 (e.g., including a mobile chassis configured to support an x-ray imaging system) including a collapsible column 604 (e.g., on which imaging components may be mounted), a search sensor 606 positioned on the column (the search sensor 606 may be a vision sensor, LiDAR, infrared sensor, etc.), a battery 610, and a charging component 608 (which may include hardware/software to support wireless charging of the battery and in some examples may be included as part of the battery management system). To position the mobile imaging system in proper proximity to a wireless charger 616, the output of the search sensor 606 may be used to navigate and position the mobile medical device platform at a charging station 612. The charging station 612 may be coupled to and/or in fixed position relative to the wireless charger 616. The charging station 612 may include a charging trigger sensor 614 (similar to charging sensor 512 of FIG. 5A), which may be an ultrasonic sensor, camera, infrared sensor, capacitive sensor, laser sensor, or other suitable proximity sensor. The output from the charging trigger sensor 614 may indicate to the charging station 612 that the mobile medical device platform is in proper position (e.g., in contact with the charging station 612) and the charging station may commence charging via the wireless charger.

In some embodiments, the charging component 608 may be independent from the wireless charger 616, and may be lowered by a drive controller in order to bring the wireless charger and charging component into closer proximity with each other. Additionally or alternatively, a wireless charger 616 may be raised in order to bring the wireless charger and charging component into closer proximity with each other, as depicted in FIG. 6B. For example, when a sensor such as search sensor 606 detects correct positioning of the mobile platform, the drive controller may automatically lower charging component 608 down to the level of wireless charger 616, or when a sensor such as charging trigger sensor 614 detects that the mobile platform is in position, charging station 612 may automatically raise wireless charger 616 to the level of charging component 608.

As with the docking process described in FIG. 5A, the battery management system, drive controller, proximity sensors, drive handle, device sensors, search sensor, charging trigger sensor, and other relevant sensors such as sensors 46 and 48 of mobile imaging system 10 in FIG. 1 may work in conjunction as an integrated system in order to achieve a smooth approach to the wireless docking station and initiation of charging. Further, it should be appreciated that as discussed in FIG. 3B, the modular nature of the battery storage component, its low positioning, and the flexibility with respect to different configurations of the battery and battery management system may facilitate customization of the mobile medical device platform for a given wireless charging station or to increase the efficiency of auto-navigation or assisted navigation and/or wireless charging.

Figure 16:
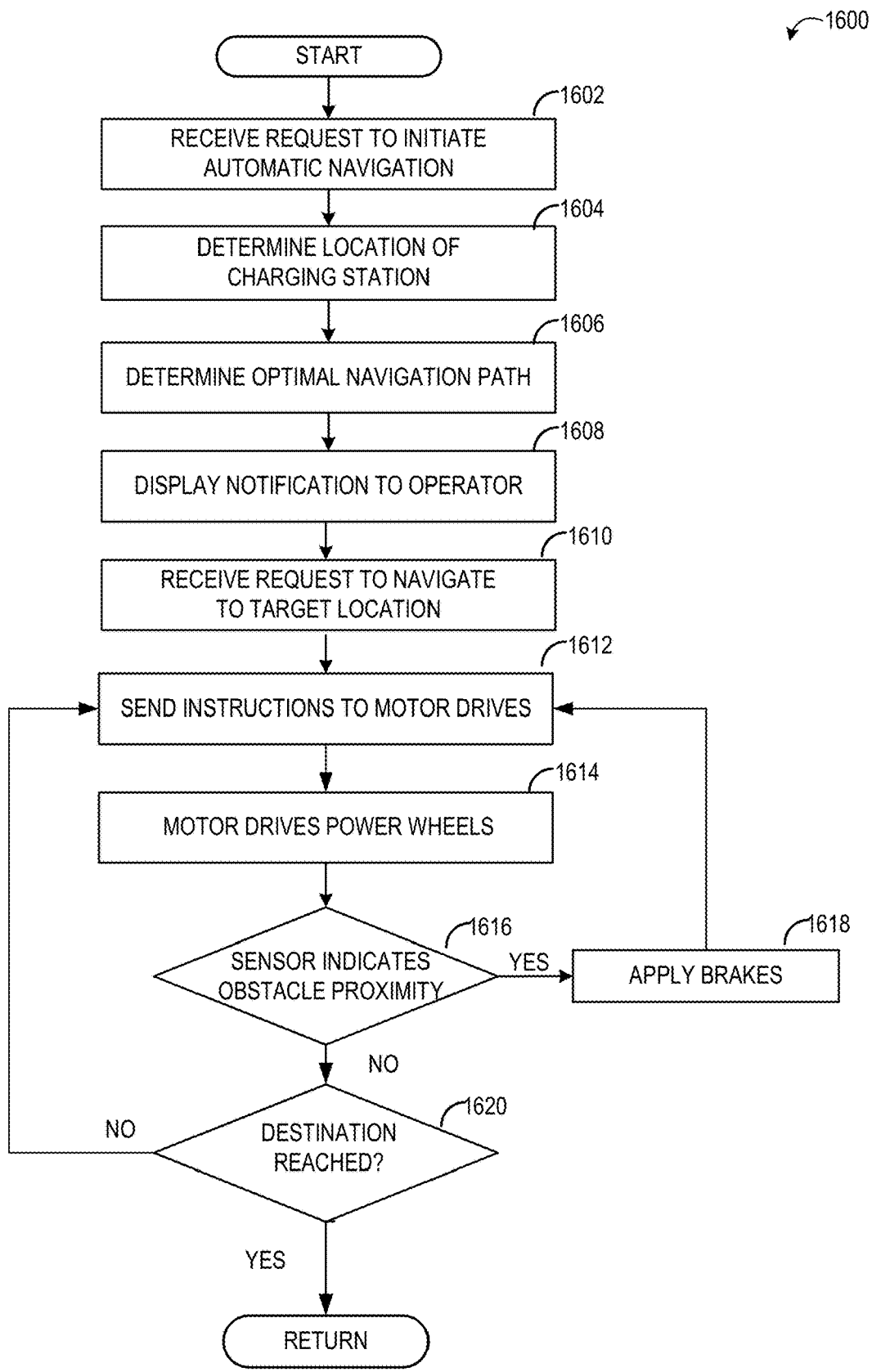
FIG. 16 is a flowchart illustrating an example method for automatic navigation of a mobile medical device platform.

A user interface (e.g., a clickable control button) may be positioned on the top cover of the mobile medical device platform, for example, as part of graphical user interface 320 of mobile platform 300 or part of operator console 14 of mobile medical device platform 12 in FIG. 2. User input to the user interface (e.g., depressing the clickable control button) may cause the mobile medical device platform to search for the charging station automatically and navigate to the charging station for charging. In some embodiments, notifications may be displayed via the user interface by a drive controller such as drive controller 50 of mobile medical device platform 12, in response to location data and other information collected by sensors such as proximity sensors 408, search sensor 606, device sensors, battery sensors, etc. An example method for automatic navigation to a charging station is shown in FIG. 16.

FIG. 6B shows a second example 601 of a wireless charging and navigation system that includes all the same components as the first example. However, rather than a collapsible column, the mobile medical device platform 602 shown in FIG. 6B includes a fixed column 605. It will be appreciated by FIGS. 6A and 6B that the sensor 606 may be positioned on the collapsible or fixed column at a position that does not change and that is not blocked by other components of the mobile medical device platform.

Thus, regardless of the specific type or configuration of the column or type or size of the medical device mounted on the mobile medical device platform, the various elements of the mobile platform including but not limited to the user interface, drive controller, force-feedback handle, omnidirectional wheels, proximity, search, and other sensors, as well as features including but not limited to the compartmentalization of space, flexible battery layout and wired and/or wireless charging, low and configurable center of gravity, and compact footprint, work together to provide a universal, flexible, and customizable solution for performance and efficiently transporting one or more medical devices under different usage scenarios. The integrated functionality of these components and features allows for the standardization of the user experience, such that the mobile medical device platform's maneuverability and the responsiveness of the drive handle remain consistent across different device installations of different sizes and weights. For example, in comparing the deployment of a medical device with a heavy C-arm that extends beyond the footprint of the mobile platform with the deployment of a small medical device centrally positioned on the platform, configurations may be obtained that minimize any driving differences from the perspective of a user.

Figure 7:
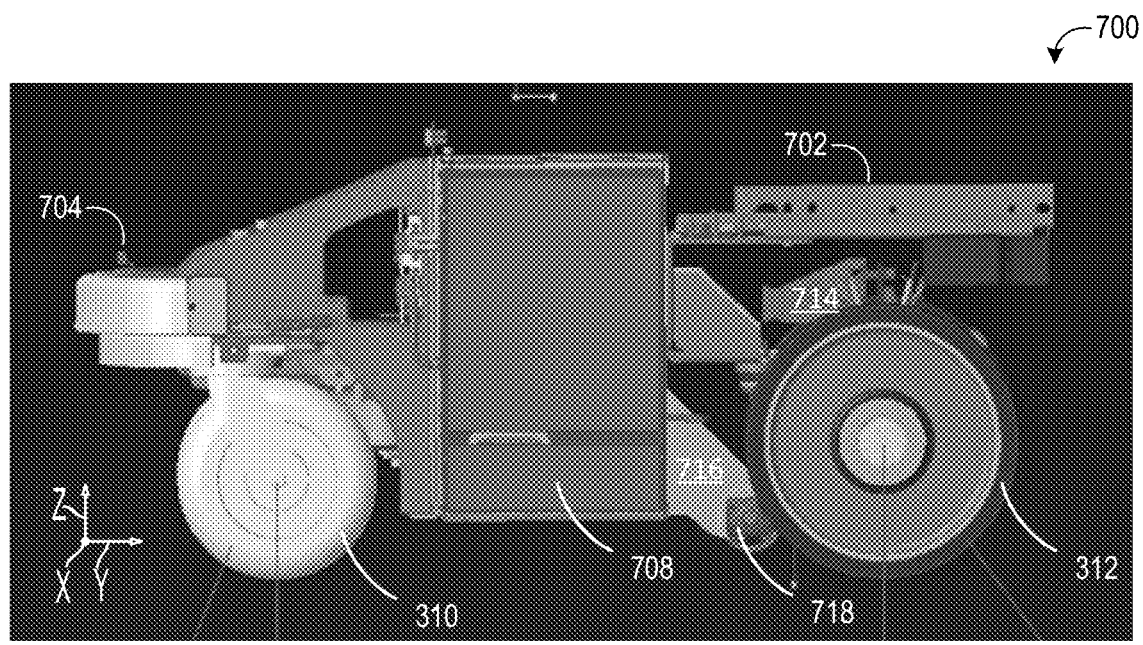
FIG. 7 shows an example mobile medical device platform viewed from the side.

Moving on to FIG. 7, lateral view 700 of the mobile platform 300 shows the spatial configuration of the elements discussed above from a side view of the mobile platform. Medical device platform 702 provides a location for mounting one or more medical devices, where a connected apparatus may be attached to a fixed or collapsible column at 704 at the front of the mobile chassis. For example, a medical device assembly such as x-ray source assembly 15 of mobile imaging system 10 may be mounted on a swivel column, as shown in in FIG. 1.

The mobile platform is powered by one or more omnidirectional rear wheels 312 described earlier, and the front wheels 310, which may comprise casters or a second pair of omnidirectional wheels for increased power and/or maneuverability. The battery/battery management system storage compartment 708 is shown in the center of the mobile platform, with access from either side as shown earlier in FIG. 3B. The weight of any component of a medical device mounted on a fixed or collapsible column installed on column base 704 may be partially offset by placement of the batteries and/or battery management system, the heaviest components of the mobile platform, in storage compartment 708. A drive controller 714 such as drive controller 50 of mobile medical device platform 12 of FIG. 1 may be positioned under medical device platform 702, which may be electronically coupled to the rear wheel drive axle to power the wheels. In some embodiments, suspension spring mount 718 may connect to the chassis via suspension interface 716.

Figure 8:
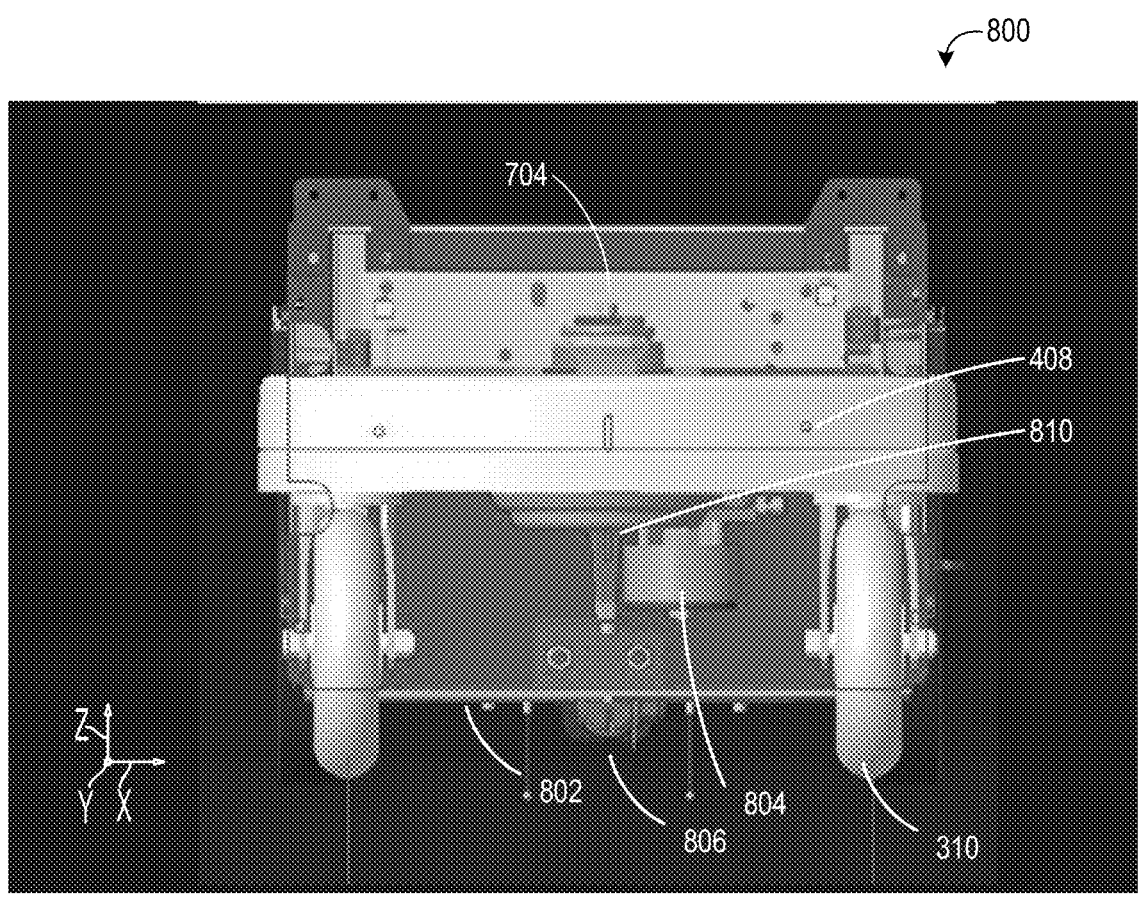
FIG. 8 shows an example mobile medical device platform viewed from the front.

In FIG. 8, view 800 shows the mobile platform 300 viewed from the front. At the center of the front of the mobile platform device column base 704 is shown, where a fixed or collapsible column can be installed which a medical device can be mounted. An encoder 804 may communicate positional and rotational data of the fixed or collapsible column from the bottom of the column base 810 to drive controller 714 in order to be aggregated with data from a plurality of sensors and control devices (e.g., user interface, drive handle) in order to generate instructions for powering the wheels according to a configurable algorithm for optimal performance and efficiency, as described in greater detail below in method 1200 of FIG. 12. The base of the chassis 802 may be positioned as low as permissible by height constraints in order to facilitate efficient wireless charging; in the illustrated embodiment, the suspension interface 716 visibly protrudes from the center of chassis 802. Proximity sensors such as proximity sensors 408 may also be located on the front of the bumper, as described in FIG. 4B.

Figure 9:
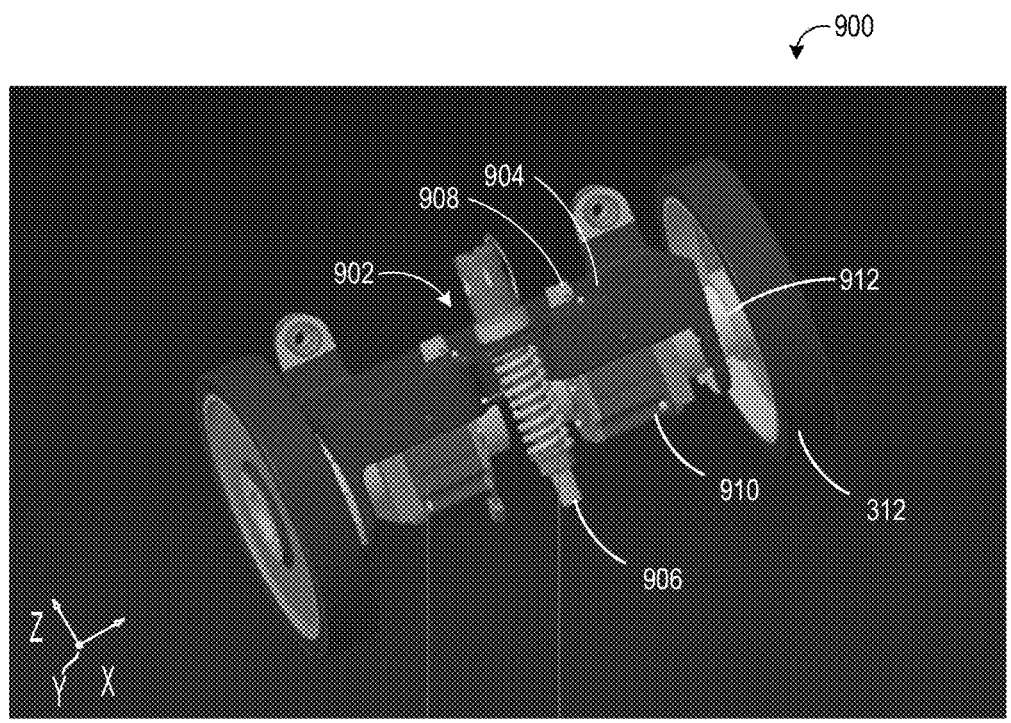
FIG. 9 shows an example suspension system in a rear omnidirectional wheel system.
Figure 10:
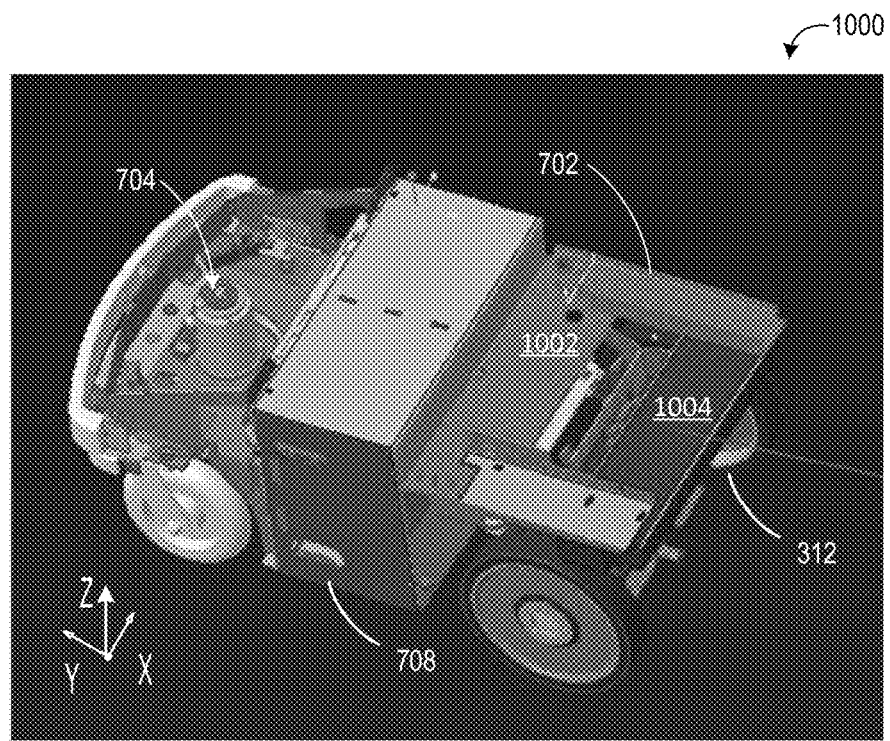
FIG. 10 shows an example mobile medical device platform viewed from above.

FIGS. 9 and 10 show the location and positioning of an example suspension system for a mobile medical device platform such as mobile platform 300 and wheeled motorized mobile medical device platform 12 of FIG. 1. FIG. 9 shows an example rear omnidirectional wheel system 900, which in an embodiment includes a rear suspension system 902 that includes a suspension brace 904 and a single centrally positioned coil spring 906 to cushion the weight of the medical device installed on the device platform directly above it. Each of the one or more powered wheels (e.g., omnidirectional wheel 312) is part of an omnidirectional wheel system that may include, among other components, a motor drive housed under suspension brace 904 and a wheel motor 910 that drives the omnidirectional wheel via split-drive axle 912. The motor drive may receive instructions for powering the wheels from a drive controller (not depicted in FIG. 9) such as drive controller 50 of mobile platform 12 in FIG. 1. The components of the split-drive axle and omnidirectional wheel system are shown in greater detail below in FIG. 14.

In an embodiment, wheel motor 910 may be an electronically commutated (EC) synchronous DC motor (e.g., brushless DC motor) powered by a 150V DC current supplied by a power supply such as battery 316 of mobile platform 300. In some embodiments, the wheel motor 910 may be controlled via a dead-man switch, whereby motion is prevented unless there is continuous user input. For example, in order to drive the mobile medical device platform, a user may have to activate a control (e.g., a button, trigger handle, etc.) such that letting go of the button, trigger, or similar control cuts power to the wheel. The power supply may be regulated by a battery management system such as battery management system 314 of mobile platform 300. The DC current may be converted into AC current that sends pulses of power to control the speed and torque of the wheel motor. The AC current may be converted from a DC power supply by an inverter, which may be a component of the battery management system or the motor drive. It should be appreciated that the brushless DC motor and related components are mentioned by way of illustration and should not be seen as limiting. In other embodiments, wheel motor 910 may be any other kind of electric motor that can operate from a portable power supply such as a battery.

A brake (not depicted in FIG. 9) may also be attached to the split-drive axle 912, which may be communicatively coupled with the motor drive. For example, a user may apply the brakes in order to stop the mobile platform via an emergency stop button such as emergency stop button 334 of platform 300, or apply brakes via a user interface such as drive handle 308 or user interface 320 of platform 300. Sensors in drive handle 308 or user interface 320 may be translated into instructions to apply the brakes by the drive controller, and subsequently transmitted to the wheel motor 910 via the motor drive. In some embodiments, the brake may be applied when the mobile medical device platform is unpowered and when drive handle input is not sensed.

Further, an encoder mounted on the split-drive axle 912 may be used to transmit pulse width modulation (PWM) signals from the split-drive axle 912 back to the motor drive, which may be transmitted back to the drive controller for displaying a notification on the operator console. If an emergency stop button such as emergency stop button 334 of platform 300 is activated to apply the brakes, the brakes may remain in a locked position until an emergency brake release switch on the operator console is pressed by an operator, sending instructions to the drive controller to resume movement. The operation of the split-drive axle and wheel system as a functional operator input is described in greater detail below in FIGS. 11-13 and 16.

In FIG. 10, top view 1000 of the mobile medical device platform shows platform 702 where one or more medical devices may be installed, located directly above rear suspension system 902. Column base 704 allows for the installment of a patient-facing component of the medical device, such that the weight of overall platform is balanced, with the heaviest components (e.g., batteries) positioned in the center and at the bottom of the platform in storage compartment 708, optionally distributed on one side or the other along with the battery management system. For example, as depicted in FIG. 1, an x-ray machine may be mounted on the mobile medical device platform, with the image processor and device console and/or graphical user interface being secured to platform 702 via rear wheel mounting bracket 1002. Platform 702 also includes counterbalance mass 1004, which serves to offset the weight of elements mounted on the front of the mobile platform, such as an x-ray tube housing with an x-ray source on an arm such as arm 32 of mobile imaging system 10 in FIG. 1 mounted to a fixed or collapsible column installed on column base 704. The power supply for the x-ray machine may be a battery, which may be stored in storage compartment 708 along with a battery management system, such as battery 316 and battery management system 314 of mobile platform 300.

Figure 11:
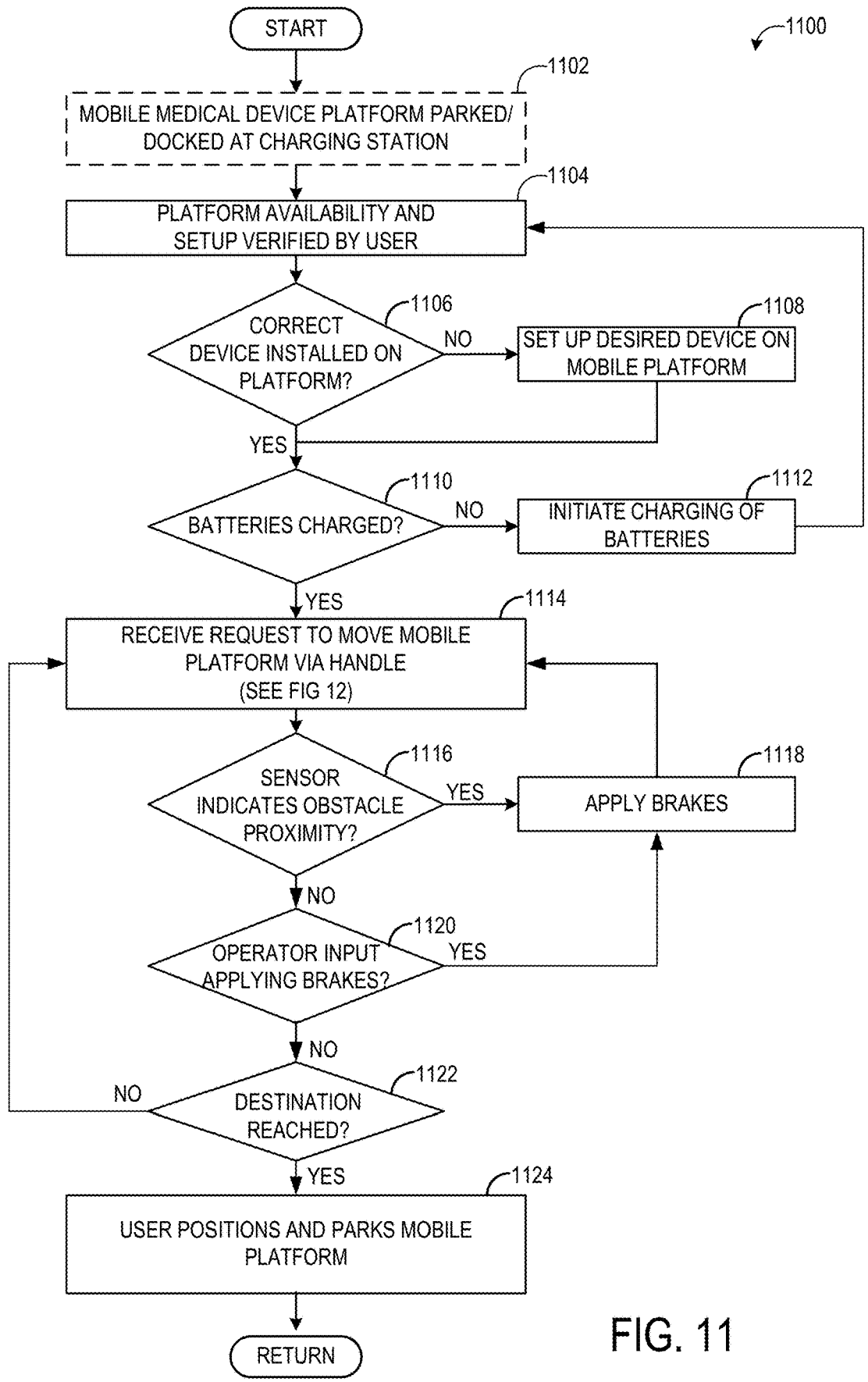
FIG. 11 is a flowchart illustrating an example method for deploying a mobile medical device platform from a charging station to a desired location.
Figure 12:
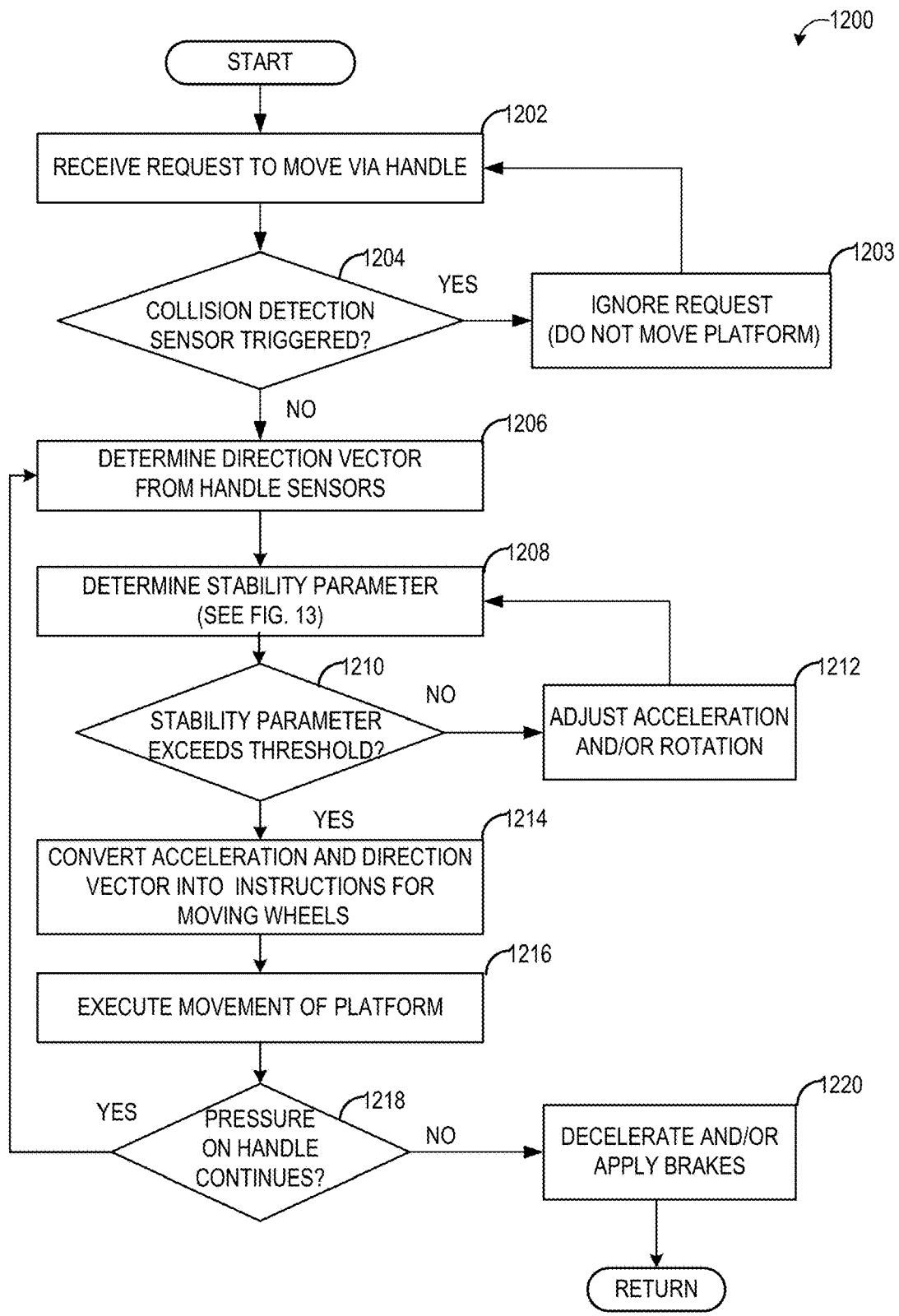
FIG. 12 is a flowchart illustrating an example method for moving a mobile medical device platform via a handle.
Figure 13:
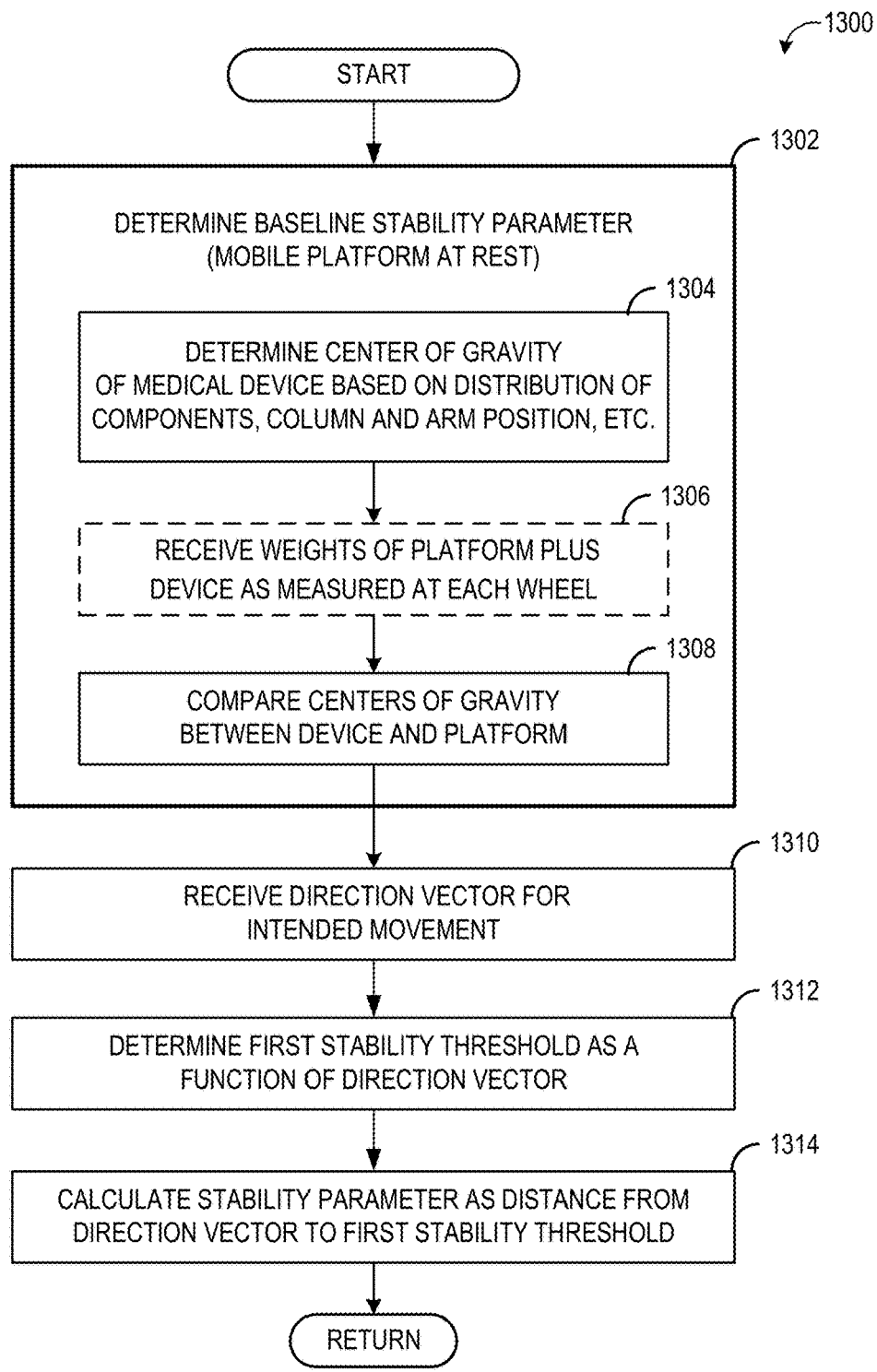
FIG. 13 is a flowchart illustrating an example method for determining limits within which a mobile medical device platform may accelerate and/or turn.

Turning now to FIGS. 11-13, the process of moving (e.g., either manually driving or auto-navigating) the mobile medical device platform from a wired and/or wireless charging station to a deployment location is illustrated via a series of nested flowcharts. In FIG. 11, example method 1100 for deployment of a mobile medical device platform where the mobile platform receives and responds to sensor input is shown. The mobile medical device platform may be initially parked or docked at a charging station, as shown in 1102. At 1104, the mobile medical device platform is checked by a user to determine whether it is ready for deployment or not. In order to be deployed, the user verifies that the appropriate device is set up on the platform and that the batteries have sufficient charge to power the device. At 1106, a determination is made whether the correct device is installed on the platform. If the correct medical device is not installed, at 1108 the medical device is set up and secured properly to the platform. If/once the correct device is properly set up on the platform, at 1110 a user determines whether the batteries have been charged. If not sufficiently charged, at 1112 the batteries are recharged and the method proceeds back to 1104 for future deployment. If the batteries have been sufficiently charged, at 1114 the user deploys the mobile platform to the desired location by manipulating a hybrid UIF drive handle such as drive handle 308 of mobile platform 300. The handle includes two or more sensors, where the difference in the sensor feedback may be used to specify a vector that indicates the proposed movement of the platform in terms of a direction and a force. This vector is translated into instructions for powering the omni-directional wheels and moving the platform, as described in mobile platform 300 of FIG. 3 and shown in greater detail below in method 1200 in FIG. 12.

Once movement has been initiated via the user interface (e.g., graphical user interface 320, drive handle 308, joystick, touch screen 332, etc.), the mobile medical device platform continues to navigate and power the wheels based on continuous user input as a function of pressure on the handle, provided that no obstacles are in its path. At 1116, the mobile platform determines whether an obstacle is present in the mobile platform's path via sensors located on the front of the mobile platform (e.g., proximity sensors 408 of FIG. 4B). If an obstacle is present at 1116, at 1118 the drive controller applies brakes to stop the mobile platform and prevent a collision, and method 1100 proceeds back to 1114 to receive further input from the drive handle. If no obstacles are present at 1116, at 1120 the mobile platform determines whether any user input to stop the mobile platform has been received via the user interface. For example, operator may activate an emergency stop button such as emergency stop button 334 of platform 300, or cease to provide force to the drive handle 308, or communicate his or her intention to stop the mobile device in other manner via an operator console such as operator console 14. If an operator has signaled his or her attention to stop the mobile vehicle at 1120, the mobile platform proceeds to apply the brakes at 1118, and method 1100 proceeds back to 1114 to receive further input from the drive handle. If the mobile platform does not receive any signal to apply brakes and/or stop the mobile platform at 1120, the mobile platform determines whether the destination has been reached. For example, an automatic navigation routing running in software in the drive controller may determine that the mobile platform has successfully reached the charging station, or an operator may cease providing any further device input. If the destination has not been reached, method 1100 proceeds back to 1114 to receive further requests for movement and navigation. If the mobile platform determines that the destination has been reached at 1122, at 1124 the operator may position and/or park the mobile platform. In some embodiments, as described above, an operator may drive the mobile platform manually via a user interface such as drive handle 38 until close proximity to a charging station such as wired charging station 504 of FIG. 5A or wireless charging station 612 of FIGS. 6A and 6B, at which point the mobile platform or the operator may trigger an automatic or assisted docking procedure.

Brakes may be applied manually by the operator via the user interface. In some embodiments, brakes may be applied automatically as result of sensors such as proximity sensors 408 indicating that the mobile platform is at risk of collision or tipping over, or in the case where the mobile platform is automatically navigating to the charging station. In some embodiments, physical brakes may not be used, and slowing or stopping the mobile platform may be accomplished by sending instructions to stop the wheels to a drive controller such as drive controller 50 of mobile platform 12 in FIG. 1.

Besides normal brake use, the mobile medical device platform may also include one or more additional features related to the brakes or movement of the wheel systems. In some embodiments, the mobile platform may have sensors that measure wheel speed and provide feedback to a drive controller, so that unintended motion is prevented. For example, the drive controller may trigger hard stops in the event of internal loop failures, excessive wheel speeds, runaway acceleration, etc. The drive controller may include a wheel spin control mechanism that prevents wheels from spinning in the event that traction is not established with a floor surface. The wheel spin control mechanism may be a software routine that executes in the drive controller and reduces wheel speed when wheel acceleration or velocity thresholds are exceeded, or a wheel spin control mechanism may trigger the application of mechanical devices such as brakes. The mobile medical device platform may include a physical locking feature whereby a user may prevent accidental motion of the system by locking the wheels. The drive controller may also have minimum and/or maximum speed thresholds that can be pre-programmed by default or re-programmed by a user depending on environmental factors such as surface type, amount of traffic, weight and/or size of a medical device, etc. Further, different minimum and maximum speed thresholds may be established for different directions, or for different conditions that may change during operation. For example, the drive controller may adjust maximum speed thresholds if sensors determine that a floor is wet, or that traffic is unusually high, etc. The mobile platform may also include physical features such as wheel protection guards that prevent cables from falling into wheel gaps, or elements that facilitate accessing the wheels for maintenance (e.g., cleaning).

FIG. 12 is a flowchart illustrating an example method 1200 for moving a mobile medical device platform via a drive handle such as drive handle 308 of mobile platform 300, from the perspective of a drive controller such as drive controller 50 of FIG. 1. Method 1200 may be carried out according to instructions stored in non-transitory memory of a controller, such as drive controller 50 of FIG. 1 and/or drive controller 714 of FIG. 7.

At 1202, the drive controller receives a request to deploy (e.g., move) the mobile medical device platform to a patient location (e.g. hospital room) from an operator via a hybrid UIF drive handle that includes two or more sensors, with at least one of the two or more sensors being installed on the left-hand side and at least one sensor installed on the right-hand side. At 1204, the drive controller determines whether a collision detection sensor (e.g., collision detection sensor 330 of mobile platform 300) has detected an object in the path of the mobile medical device platform. If the collision detection sensor has detected an object in the path of the mobile platform at 1204, the drive controller decelerates the mobile platform to a halt, and then proceeds back to 1202 to receive further requests to move via the drive handle. As long as the collision detection sensor detects an object at 1204, requests to move via the drive handle are received but ignored at 1203, whereby requests to move cannot proceed to 1206 until the collision detection sensor no longer detects an object or until the automatic halting of the platform has completed. In some embodiments, the automatic halting of the mobile platform may be deactivated manually by a user when the path to be taken by the mobile platform has been cleared of obstacles. In other embodiments, the automatic halting of the mobile platform may be deactivated if/when sensors indicate the absence of any obstacles in the path of the mobile platform. The examples mentioned above are for illustrative purposes, and other types of collision detection mechanisms may be included in a non-limiting fashion within the scope of this disclosure.

When the collision detection sensor is deactivated, at 1206 the drive controller determines a direction vector from the request issued via the handle sensors. The drive controller converts the data from the left-hand and right-hand handle sensors into a direction vector with two dimensions (e.g., a direction on the ground plane and a magnitude of force to be applied as acceleration). For example, an operator may apply equal force to both sides of the drive handle, in a forward direction, to indicate forward movement of the mobile platform. Alternatively, an operator may apply force to one side of the drive handle in a forward direction, and equal force to the other side of the drive handle in a backward direction, to indicate rotation in place. Example interpretations of different pressure combinations on the drive handle are shown in more detail in FIG. 15.

Once the user's pressure on the drive handle has been interpreted by the drive controller as a direction vector, at 1208 the drive controller proceeds to assign a stability parameter to the direction vector that indicates whether or not executing the instructions for movement could destabilize the mobile platform. For example, forceful pressure to one side of the drive handle by the drive controller, indicating rapid acceleration and a turn to one side, could cause the mobile platform to tip over. It should be appreciated that the term "acceleration" herein may refer to either positive or negative acceleration (e.g., deceleration or braking). In an embodiment, the stability parameter may be a value between −1 and 1, where negative values indicate that the intended movement may destabilize the mobile platform, positive values indicate that the intended movement will not destabilize the mobile platform, the magnitude of the parameter may indicate a degree of confidence, and 0 may indicate that the intended movement is on a boundary between stability and instability.

In an embodiment, a stability parameter may be determined by comparing a direction vector to a first stability threshold which, if exceeded, could cause the mobile platform to become destabilized. For example, the drive controller may calculate stability thresholds as a function of the direction vector by assessing weight and positional factors of a medical device installed on the mobile platform and looking up acceptable acceleration and rotation parameters for different configurations and speeds (determined by the manufacturer or via testing, etc.). Acceptable first stability thresholds for different mobile platform configurations may be stored in non-transitory computer memory, and calculated by the drive controller as a function of a given direction vector. Weight and positional factors may include the weights of the different components of the medical device installed on the platform as measured by weight sensors located on the platform, at the wheels, or at any other location on the chassis, and/or any combination of sensor data from proximity sensors, battery management sensors, device configuration sensors such as sensor 46, push sensor 62, and pull sensor 64 of mobile medical device platform 12 in FIGS. 1 and 2, and/or any other sensors of the mobile platform. An example method by which an acceptable first stability threshold value and a subsequent stability parameter may be determined is shown in further detail in FIG. 13.

At 1210, the drive controller determines whether the stability parameter determined at 1208 exceeds a second stability threshold value, in order to determine whether to apply the instructions for moving the omnidirectional wheels based on the direction vector at 1214, or to modify the instructions for moving the omnidirectional wheels at 1212. In an embodiment, the second stability threshold value may be pre-programmed into the drive controller based on hospital policies, as described in an example below.

If the second stability threshold is not exceeded at 1210, at 1212 the drive controller may reduce the intended acceleration and/or rotation in order to ensure the stability of the mobile platform, then proceeding back to 1208 to calculate a new stability parameter. The degree to which the acceleration may be modified in each iteration and the precision of the calculation of the stability parameter, including any transformations (e.g., sinusoidal, etc.) used in the first stability threshold function, may be configured by the manufacturer, or by a user, a hospital administrator, or any other relevant authority.

As an example, at 1208, the drive controller may determine a stability parameter value of 0.8 according to the procedure described in the previous paragraphs and described below with respect to FIG. 13. A stability parameter of 0.8 may indicate that the combination of intended acceleration and rotation fall within a first stability threshold, meaning that the intended movement is not likely to destabilize the mobile platform, with degree of confidence of 0.8 (80%). The drive controller may then compare the stability parameter value of 0.8 calculated at 1208 with a second, pre-programmed stability threshold value of 0.9, which may indicate that according to hospital policies, movement of the mobile platform should only be executed when the intended movement is determined to be stable with a degree of confidence above 0.9 (90%). Since the stability parameter (0.8) does not exceed the second stability threshold value (0.9), the intended movement may be adjusted by reducing the intended acceleration.

Once a direction vector that results in a stability parameter that exceeds the second stability threshold is determined according to the above procedure, the drive controller converts the direction vector into instructions for powering the omnidirectional wheels at 1214, and at 1216 the drive controller sends the instructions to the motor drives of the relevant omnidirectional wheels in order to execute the movement of the mobile platform accordingly.

At 1218, the drive controller determines whether requests to move the mobile platform are still being received via pressure on the drive handle. If there is a request to alter the mobile platform's speed or direction (e.g., pressure on the handle continues), the method proceeds back to 1206 to process the user input via the handle sensors. Alternatively, if user input indicating movement of the mobile platform ceases (e.g., if the pressure does not continue), at 1220 the drive controller sends instructions to the motor drive to decelerate the mobile platform via the wheel motor (e.g., to a stop) and/or apply the brakes as appropriate to bring the mobile platform to a halt.

It should be appreciated that as described earlier, in some embodiments the drive controller may receive input from an alternative control device other than the drive handle, such as a graphical user interface, touch screen, joystick or from a computer program executing within the drive controller for automatic navigation, or via any other alternative mechanism for moving the mobile platform.

FIG. 13 shows an example method 1300 for determining a stability parameter for a given direction vector received from a drive handle such as drive handle 308 of mobile platform 300, from the perspective of a drive controller such as drive controller 50 of mobile platform 12 in FIG. 1. As described above, the stability parameter is a numerical indication of how much an intended movement might destabilize a mobile medical device platform when accelerating and/or turning, to be applied as part of method 1200 above. Method 1300 may be executed as a subroutine within software running on the drive controller, or executed as a separate software component on a separate processor.

At 1302, the drive controller determines a baseline stability parameter for the mobile platform at rest. In an embodiment, a baseline stability parameter may be calculated based on a comparison of the center of gravity of the mobile medical device platform and the center of gravity of a medical device installed on the platform. For example, if an x-ray source is mounted on an arm such as arm 32 on column 16 of mobile imaging system 10 in FIG. 1, the center of gravity calculations will vary depending on the rotation and position of the arm and whether column 16 is collapsed or fixed. If the arm is extended beyond the perimeter of the platform, the distance between the center of gravity of the x-ray source and the center of gravity of the mobile platform may indicate that the mobile platform cannot be effectively moved at certain speeds or in certain directions, or not at all. The baseline stability parameter may also be calculated based on other factors, such as a weight of the medical device, positioning of the medical device on the platform, a height of the medical device, a distance between the center of gravity and the ground, width or length center measurements, counterbalance mass, symmetricity, etc.

In an embodiment, in order to determine a baseline stability parameter for a configuration of the mobile platform, at 1304 the drive controller calculates the center of gravity of the medical device based on the distribution of the device elements on the platform, column, and arm. In some embodiments, the center of gravity of the medical device under various different arm and column configurations may be pre-programmed into the drive controller. The center of gravity may be in a single dimension, two dimensions, or three dimensions (e.g., x, y, and z). Additionally or alternatively, at 1306 the drive controller may measure the weight of the platform and device together at different locations, for example, at the base of the mobile platform at each wheel, which may aid the controller in determining the center of gravity of the medical device. For example, the difference in weight measurements between one side of the mobile platform and the other side of the mobile platform may indicate the offset between the center of gravity of the medical device and the center of gravity of the mobile platform in the X-Y plane, while the vertical offset (Z plane) may be function of the fixed height of the medical device. Medical device height measurements may be input manually by an operator in advance, or they may be stored in computer memory accessible by the processor in the drive controller at the time of making the calculation.

At 1308, the center of gravity of the medical device is compared to the center of gravity of the mobile platform. For example, a distance between the two centers of gravity may be calculated and expressed in three dimensions (e.g., X, Y, Z) from the reference point of the center of gravity of the mobile medical device platform. Thus, a center of gravity comparison can be used to generate a baseline stability parameter, for example by measuring Euclidian distance between the centers of gravity, or a similar calculation.

At 1310, the drive controller receives a direction vector for new movement from the drive handle, based on the drive handle sensors. The direction vector received from the user is separated into its two components, desired rotation and acceleration. At 1312, the drive controller determines a first stability threshold for one of the components as a function of the other component, based on the current speed of the mobile platform and a given baseline stability parameter determined at 1302. For example, for a mobile platform with a given configuration traveling at a given speed, the drive controller may determine a stability threshold for acceleration (dependent variable) based on a given desired rotation (independent variable), or the drive controller may determine a stability threshold for rotation (dependent variable) given a desired acceleration (independent variable). In an embodiment, the drive controller may determine a first stability threshold by consulting a lookup table stored in the non-transitory memory of the drive controller. The lookup table may be created in advance by the mobile platform manufacturer, or by a hospital administrator, standards organization, or similar authority based on testing with different medical devices, configurations, operating conditions, etc. Additionally, which variable to use as the independent variable and which variable to use as the dependent variable may differ according to circumstances, and may also be determined as result of testing.

For example, the drive controller may determine a baseline stability parameter of 0.6 for a given configuration of the mobile platform at 1302, indicating that the mobile platform is stable at rest. The drive controller may determine a current speed of the mobile platform of 0.5 meters per second via sensors located at the motor, wheels, or other location on the mobile platform. The drive controller may receive a direction vector from the drive handle at 1310, comprising an intended rotation component of 45 (e.g., indicating a 45-degree turn to the right) and an intended acceleration component of 0.3 (e.g., indicating a 30% increase in velocity). The drive controller may consequently determine an acceleration threshold of 0.5 as a function of the other three variables (e.g., baseline stability parameter, mobile platform velocity, and intended rotation) by consulting a first stability threshold lookup table. As the determined acceleration threshold of 0.5 (e.g., permitted acceleration of up to 50%) is above the intended acceleration of 0.3, the drive controller may determine that it may execute the intended direction vector without tipping the mobile platform over.

At 1314, the drive controller calculates a stability parameter specific to the specific mobile platform configuration and velocity to be used in method 1200 of FIG. 12. The stability parameter may be based on the difference between the intended acceleration and the threshold acceleration generated at 1314, and may indicate a degree of confidence that the intended acceleration will or will not tip the mobile platform over. In the above example, the drive controller may determine a stability parameter of 0.95 (e.g., indicating a high degree of confidence that the mobile platform will not tip over) by subtracting the intended acceleration of 0.3 from the acceleration threshold of 0.5 determined by consulting the lookup table and applying a transformation to return a number between −1 and 1.

Figure 14:
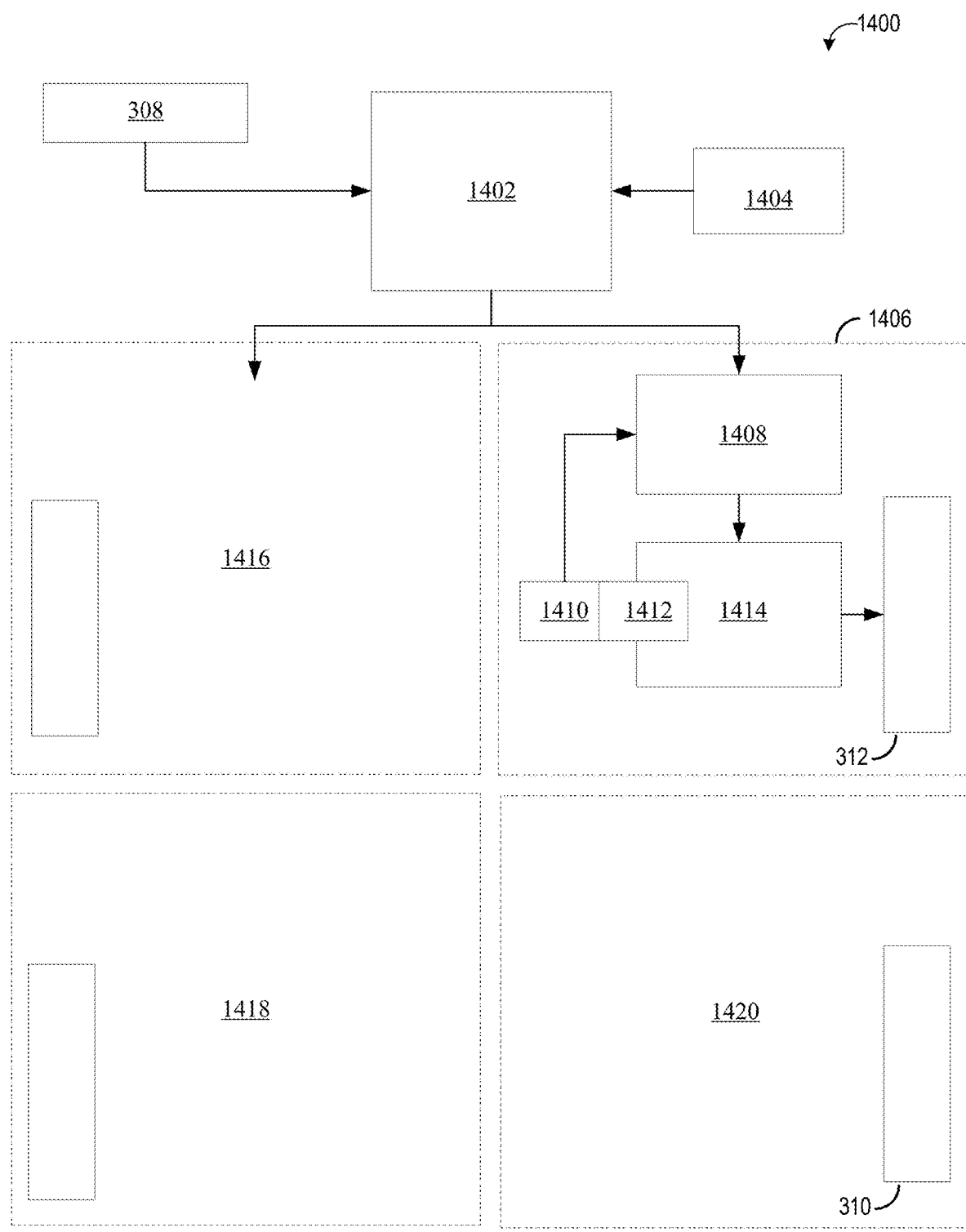
FIG. 14 is a block diagram illustrating the components involved in powering omnidirectional wheels.

Moving on to FIG. 14, schematic diagram 1400 shows an example motor drive architecture for a mobile medical device platform such as mobile medical device platform 12 of FIG. 1. As discussed earlier, a drive controller 1402 receives user input from a drive handle such as drive handle 308 of mobile platform 300. The drive controller translates the input into instructions that are sent to one or more omnidirectional wheel systems 1406, 1416, 1418, and 1420. The components of each wheel system are shown in omnidirectional wheel system 1406. In each omnidirectional wheel system there is a motor drive 1408, which controls a motor 1414 for the corresponding omnidirectional wheel 312. In some embodiments, a brake 1412 may be installed on motor 1414, which may be used to stop the mobile platform. In other embodiments, stopping the mobile platform may be accomplished via instructions sent to the motor 1414. As described above in FIG. 9, an encoder 1410 may also transmit pulse width modulation (PWM) signals back to the motor drive, for greater control over the motor.

Figure 15:
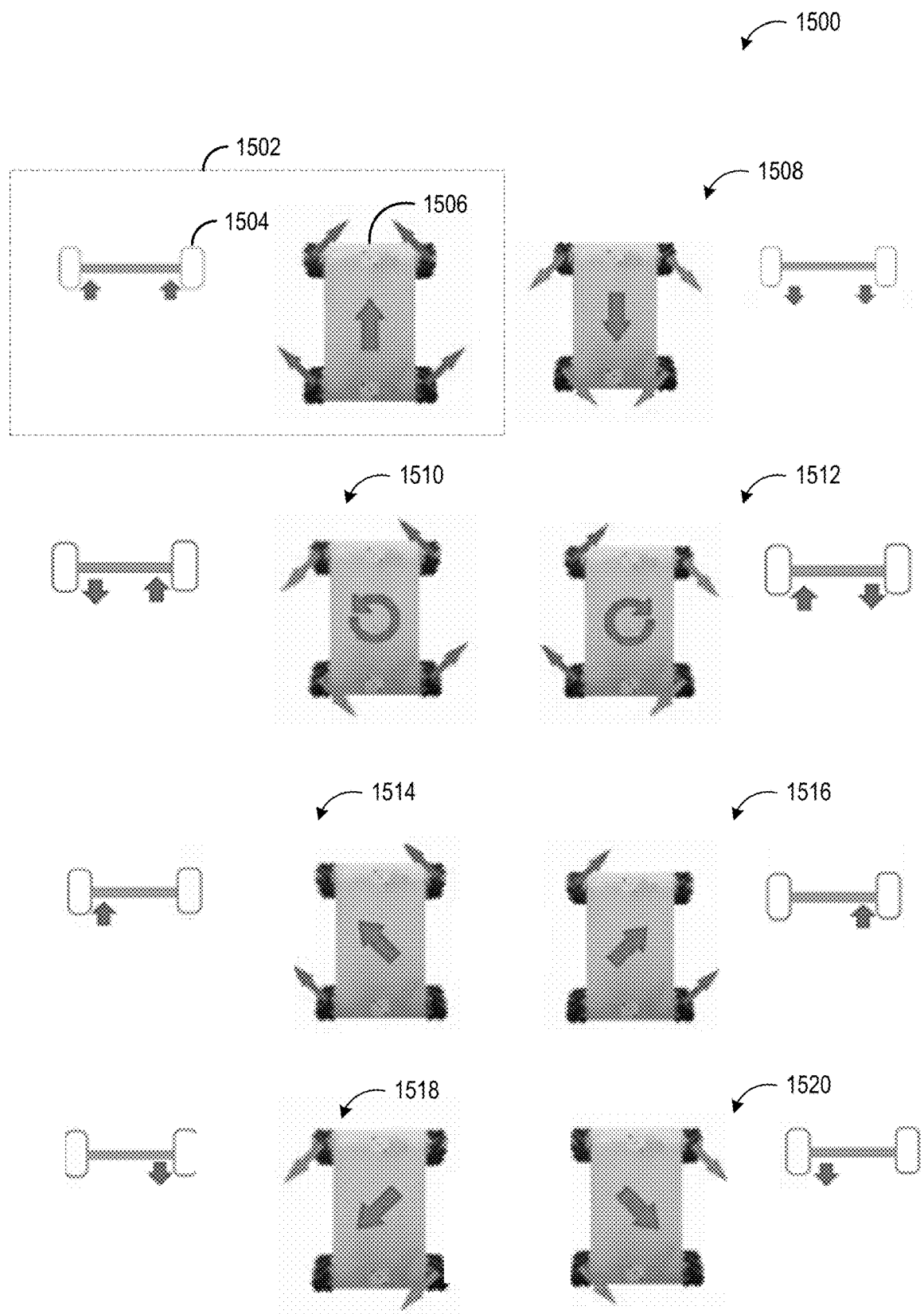
FIG. 15 shows example pairings of drive handle input and the corresponding wheel movements for Mecanum or double-cone omnidirectional wheels.

FIG. 15 shows example set of input-wheel movement pairings 1500, which illustrates in detail how different combinations of user input, via pressure on a drive handle such as drive handle 308 of mobile platform 300, may be translated into instructions to power two or more double-cone Mecanum wheels. The example set of input-wheel movement pairings 1500 comprises eight different pairings. The examples are not exhaustive and further a system may use less than the eight pairings shown. Further, while the examples show approximately 45 degree angles, the actual angle may correspond to the actual commanded forces or joystick inputs.

Pairing 1502 shows example drive handle input for powering a mobile platform forward; pairing 1508 shows example drive handle input for powering a mobile platform backward; pairing 1510 shows example drive handle input for rotating a mobile platform in a counterclockwise direction; pairing 1512 shows example drive handle input for rotating a mobile platform in a clockwise direction; pairing 1514 shows example drive handle input for powering a mobile platform diagonally forward and to the left; pairing 1516 shows example drive handle input for powering a mobile platform diagonally forward and to the right; pairing 1518 shows example drive handle input for powering a mobile platform diagonally backward and to the left; and pairing 1520 shows example drive handle input for powering a mobile platform diagonally backward and to the right.

For example, as shown in input-wheel movement pairing 1502, forward pressure applied to both sides of drive handle 1504 may be translated into forward rotation of four omnidirectional double-cone Mecanum wheels in order to drive mobile platform 1506 in a forward direction. It should be appreciated that while Mecanum wheels rotate forward and backward as normal wheels do, the rotating surface of the wheels also has a plurality of powered rollers oriented diagonally with respect to the direction of the wheel, such that as the mobile platform moves linearly forward and backward, the diagonal rollers may act collectively to also move the mobile platform in a lateral direction. This is accomplished by positioning the diagonal rollers at different orientations depending on the wheel, such that the X and Y components of the motion of the different rollers can be summed up across all wheels to generate motion in any direction in the X-Y plane (e.g., 360 degrees of freedom).

Moving on to FIG. 16, an example method 1600 to be carried out on a mobile medical device platform for automatic deployment and navigation to a target location (e.g., a charging station) is shown. As discussed above, in some cases a mobile medical device platform may self-navigate along a given layout, for example hospital corridors, to return automatically to a charging station or storage location. Automatic navigation may save time for medical personnel, freeing them up to attend to other healthcare or patient-facing tasks. Further, some devices may be difficult for an operator to drive manually, due to size or weight constraints.

At 1602 the mobile medical device platform receives a request to initiate automatic navigation. For example, an operator may select an option or activate a button on a user interface (e.g., user interface 44 or operator console 14 of medical device system 10 in FIG. 1) to direct the mobile medical device platform to search for one or more charging stations, storage areas, or other target locations. Target locations may be specified in advance and programmed into a drive controller such as drive controller 50 of mobile medical device platform 12 in FIG. 2, or in other cases the mobile medical device platform may be programmed to identify any target location via a signal emitted by a transceiver at the target location, or by other similar means. At 1604, the mobile medical device platform determines the location of the charging station (or target location) to which it will navigate. In some embodiments, the mobile medical device platform may select an optimal target location from a selection of candidate target locations according to an algorithm programmed into the drive controller. For example, the mobile platform may be configured to select the charging station that is nearest to the platform and not already being used. In other embodiments, the mobile medical device platform may display the various candidate target locations as options on a graphical user interface from which an operator may select the most appropriate option.

Once the target location has been selected at 1604, at 1606 the mobile medical device platform determines the optimal path for navigating to the target location. In some embodiments, the optimal path may be determined by an expert system defined by algorithms programmed into the drive controller in advance (e.g., the most direct path). In other embodiments, the mobile medical device platform may dynamically select the optimal path based on sensor input while navigating along the path. For example, the mobile medical device platform may select different navigation paths (e.g., hospital corridors) depending on human traffic or other time-dependent data received by sensors on the mobile medical device platform, including vision sensors, LiDAR, infrared sensors, or any other suitable type. In other embodiments, the mobile medical device platform may receive radio or other signals transmitted from a distance that may be generated automatically or by a remote operator that aid the mobile medical device platform in selecting an appropriate navigation path.

At 1608, the mobile medical device platform may display a notification to an operator on an operator console such as operator console 14 of mobile medical device system 10, requesting confirmation or verification of the selected path. Additionally or alternatively, the mobile medical device platform may allow the operator to manually select the optimal path. For example, the mobile medical device platform may detect two wired and/or wireless charging stations at different locations that are both available, and prompt an operator to determine which location to select for the mobile medical device platform to navigate to. At 1610, the mobile medical device platform receives the request to navigate to the target location from the operator via the operator console. Upon receiving the request, at 1612 the drive controller sends the relevant instructions to motor drives such as motor drive 1408 of schematic diagram 1400 in FIG. 14. At 1614, the motor drives power the omnidirectional wheels in order to initiate movement, as shown in FIG. 15.

At 1616, the mobile medical device platform determines whether any sensors (e.g., proximity sensors 406 of FIG. 4) indicate any obstacles in the path. If an obstacle is present at 1616, at 1618 the mobile medical device platform applies the brakes and method 1600 proceeds back to 1612 to receive further instructions in order to continue its navigation. In some embodiments, an expert system programmed in the drive controller of the mobile medical device platform may determine a series of rules to follow when it obstacles present. For example, the mobile medical device platform may delay movement in order to see if the obstacle leaves its path, or may determine a different path to follow to navigate to the target location. If the mobile platform is able to continue along its path and no obstacles are at 1616, at 1620 the mobile medical device platform determines whether or not the mobile platform has reached its destination. If the mobile platform has reached the intended destination, method 1600 returns. If the mobile platform has not reached its intended destination, method 1600 proceeds back to 1612 to process further navigation instructions.

As an example, the mobile platform may self-navigate to a charging station such as charging station 504 of FIG. 5 in order to recharge its battery. Once the charging station has been reached, the mobile platform may self-navigate into position, for example, in order to dock with the station via a docking mechanism such as docking mechanisms 514 and 516 of FIG. 5A. Self-navigation to the docking mechanism may also be facilitated by a docking sensor such as docking sensor 518. Once the mobile platform has docked, charging may be initiated. Alternatively, the mobile platform may self-navigate to a parking location, at which point it may be put into a parking state (e.g., powered down, brakes activated, etc.).

Figure 17:
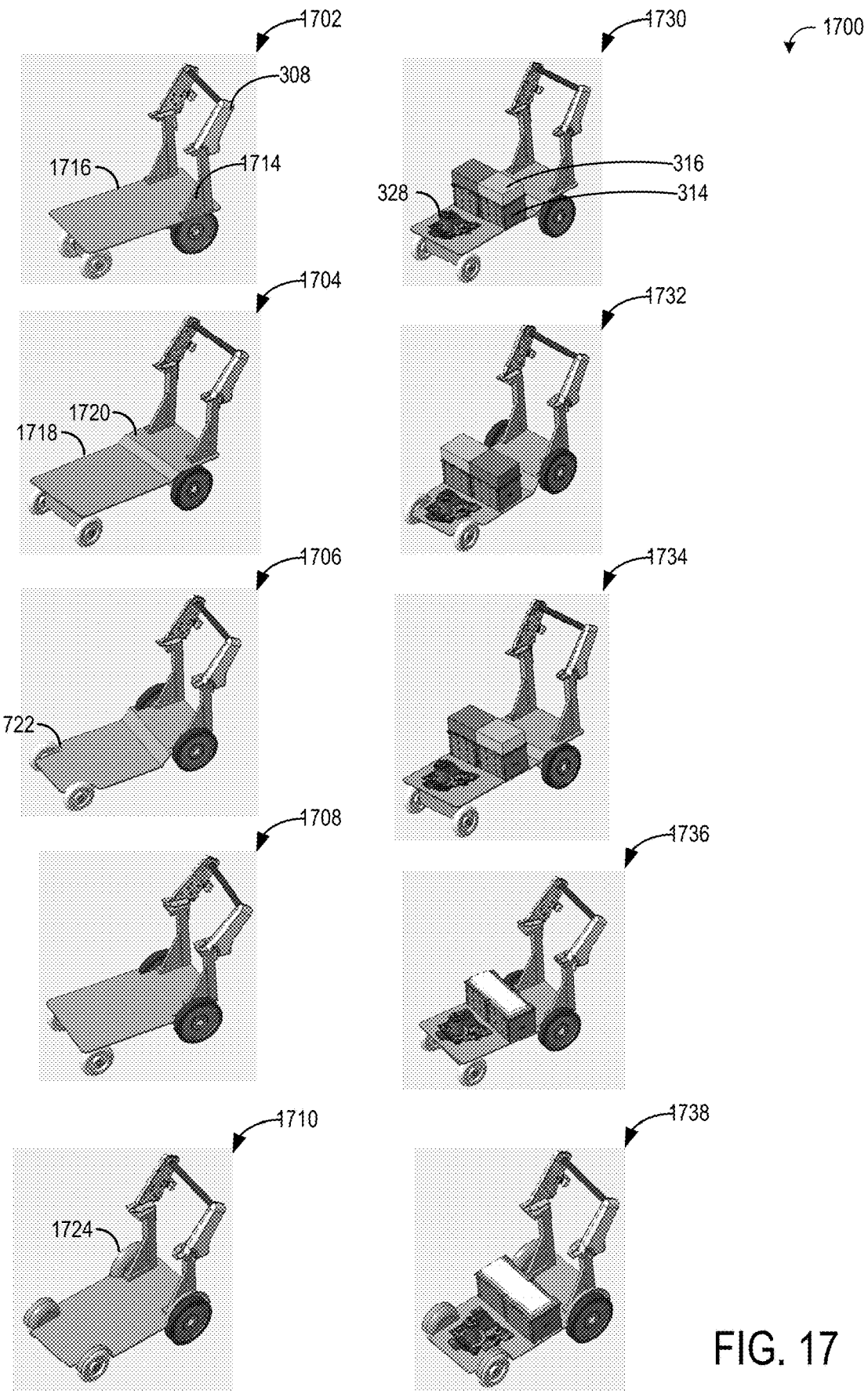
FIG. 17 shows an example of different skateboard chassis configurations.

The configuration of the mobile medical device platform is highly customizable, depending on the needs of the medical unit or service using it. As such, alternative configurations for the mobile platform based on various skateboard chassis configurations are shown in FIG. 17. In contrast to the chassis depicted in FIGS. 7-10, a skateboard chassis comprises a flat platform upon which components such as a battery and battery management system, column base, counterbalance, etc. may be arranged in a flexible and customizable fashion.

FIG. 17 shows image pairs for five different skateboard chassis configurations 1702, 1704, 1706, 1708, and 1710, each of which includes a skateboard chassis platform 1716 and a hybrid UIF user interface drive handle 308 of FIG. 3 for driving the mobile medical device platform, where drive handle 308 is attached to the skateboard chassis via triangular bracket 1714. Elevated flat chassis 1702 shows a skateboard chassis in which the platform 1716 is elevated for maximum clearance, with the omnidirectional wheel systems located entirely below the platform. Lowered flat chassis 1704 shows a skateboard chassis in which a forward skateboard chassis portion 1718 has been lowered with respect to a rear skateboard chassis portion 1720, for example, to lower the height of elements such as a fixed or collapsible column mounted on the front of the platform. As with elevated flat chassis 1702, all omnidirectional wheel systems are located underneath the skateboard chassis.

In contrast, skateboard chassis 1706, 1708, and 1710 are skateboard chassis configurations in which some or all of the omnidirectional wheels are positioned on the side of the skateboard chassis platform. Deep lowered flat chassis 1706 has a skateboard chassis with a forward portion that has been lowered below the level of lowered flat chassis 1704, where both the front wheels and the back wheels are inset and extend vertically above the level of the platform, as shown at wheel inset 1722. In contrast, wheel out flat chassis 1708 has a flat platform with rear wheels that are inset and extend vertically above the level of the platform as with deep lowered flat chassis 1706, and front wheels positioned below the platform as with lowered flat chassis 1704. Wheel out and lowered flat chassis 1710 shows a flat skateboard chassis at a low position, with all four wheels inset and extending vertically above the level of platform. Wheel out and lowered flat chassis 1710 also features protective wheel guards such as protective wheel guard 1724, which may prevent cables or other objects from falling into the gap between the wheels and the mobile platform.

Loaded chassis 1730, 1732, 1734, 1736, and 1738 show skateboard chassis 1702, 1704, 1706, 1708, and 1710, respectively, with a battery management system 314, battery 316, and column base 328 of FIG. 3 installed on the skateboard chassis. In this way, a skateboard chassis design allows for a flexible arrangement of other mobile medical device platform components (e.g., batteries, BMS, drive controller, counterbalance, etc.). Further, by configuring the wheels either underneath or on the side of a skateboard chassis, different platform heights may be obtained, including platforms where different portions are at different heights.

Thus, a mobile medical device drive platform is provided herein that includes a battery within a chassis that may be flexibly configured, with an omnidirectional wheel system, a hybrid user interface that enables 360 degree range of movement, along with wired or wireless charging option. In some embodiments, the mobile medical device drive platform may include batteries with a battery management system, with docking option for wired charging and sensor to identify when the mobile platform has reached the wired charging station. In other embodiments, the mobile medical device drive platform may include batteries with a battery management system, with wireless charging and sensor to identify when the system has reached a wireless charging station. In still other embodiments, the mobile medical device drive platform may include an automatic search option to reach out to wired or wireless charging station with LiDAR technologies and return back to a requested or target destination (e.g., using artificial intelligence).

The mobile medical device drive platform may include an auto assist mode, where the mobile medical device drive platform has a maneuvering assist and collision detection system, which helps to controls the speed when an obstacle is nearing, while driving or parking (reducing the speed to a user acceptable speed and stopping when about to collide with an object). The mobile medical device drive platform may include remote operation or an automated guided vehicle (AGV) in hospital corridors via a coded guide path with AI technology, whereby the mobile medical device drive platform is sent to the desired room by an operator via WiFi.

The mobile medical device drive platform described herein may provide several advantages, including automatic wired or wireless charging station search and navigation when triggered, no charging cable issues or wire damage, easy bedside positioning and parking, easy maneuvering while turning right, left, reverse, and sideways, and collision avoidance technology during navigation. Further, the platform may be used for one or more medical devices, such as surgery systems, ultrasound, x-ray, anesthesia systems, or others. The common platform design for different imaging modalities/medical devices may enable standardization with regard to mobile medical systems, which may lower costs. The automatic charging capabilities may reduce the workflow for users.

FIGS. 1-10, 14, 15, and 17 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

An example provides for a mobile platform including a chassis configured to house one or more medical devices; an omnidirectional wheel system coupled to the chassis, a battery housed in the chassis; the battery configured to supply power to drive the omnidirectional wheel system and/or supply power to operate the one or more medical devices and a battery management system housed in the chassis, where the battery management system is configured to facilitate wired and/or wireless charging of the battery. In a first example of the mobile platform, wherein the omnidirectional wheel system is a first omnidirectional wheel system of at least two omnidirectional wheel systems, the chassis includes a drive controller configured to automatically control the at least two omnidirectional wheel systems. In a second example of the mobile platform, which optionally includes the first example, the drive controller is configured to automatically control the at least two omnidirectional wheel systems to move the mobile platform to a charging station. In a third example of the mobile platform, which optionally includes one or both of the first and second examples, the mobile platform comprises a controller configured to receive inputs from a user and control operation of the omnidirectional wheel system in response thereto. In a fourth example of the mobile platform, which optionally includes one or more of each of the first through third examples, the controller includes instructions stored in memory to determine a stability parameter of a current configuration of the mobile platform and adjust output of the omnidirectional wheel system in response to the determined stability parameter. In a fifth example of the mobile platform, which optionally includes one or more of each of the first through fourth examples, the mobile platform includes a swivel column. In a sixth example of the mobile platform, which optionally includes one or more of each of the first through fifth examples, the mobile platform includes a forward wheel set and a rearward wheel set and the omnidirectional wheel system is part of the forward wheel set or the rearward wheel set, and the battery is positioned between forward and rearward wheel sets, and rearward of the swivel column. In a seventh example of the mobile platform, which optionally includes one or more of each of the first through sixth examples, the mobile platform includes a rear suspension system including a brace and a single centrally positioned coil spring. In an eighth example of the mobile platform, which optionally includes one or more of each of the first through seventh examples, the omnidirectional wheel system includes a motor drive housed under the suspension brace and a wheel motor that drives the omnidirectional wheel via a split-drive axle. In a ninth example of the mobile platform, which optionally includes one or more of each of the first through eighth examples, the mobile platform includes a handle with first and second force-sensing regions positioned along the handle to engage each hand of a user. In a tenth example of the mobile platform, which optionally includes one or more of each of the first through ninth examples, the mobile platform includes a controller receiving inputs from the user's hands through one or more of the force-sensing regions on the handle and control operation of the omnidirectional wheel system in response thereto. In an eleventh example of the mobile platform, which optionally includes one or more of each of the first through tenth examples, rotation of the omnidirectional wheel in the omnidirectional wheel system and an angle of drive torque of the omnidirectional wheel are both responsive to sensed force from the user's interaction with the first and second force-sensing regions of the handle.

An example provides for a method of operation of a mobile platform driven by an omnidirectional wheel system having a chassis configured to house one or more medical devices, including moving the mobile platform by driving one or more omnidirectional wheels with an electric motor and a battery responsive to a user input physically interfacing with the mobile platform; wirelessly charging the battery; and controlling the moving of the mobile platform based on a configuration of a medical device coupled to the platform. In a first example of the method, the controlling of motion includes limiting of motion based on a determined stability parameter of the mobile platform. In a second example of the mobile platform, which optionally includes the first example, the stability parameter includes a center of gravity of the platform and medical device in combination. In a third example of the mobile platform, which optionally includes one or both of the first and second examples, the moving of the mobile platform is in response to sensed forces from the handle, the moving including driving the omnidirectional wheels to move both longitudinally and laterally. In a fourth example of the mobile platform, which optionally includes one or more of each of the first through third examples, the medical device includes an arm, wherein controlling motion includes limiting a speed of the mobile device platform in a specified direction based on an arm position.

An example provides for a mobile platform, including a chassis configured to house one or more medical devices, a forward wheel set coupled to the chassis, a rearward wheel set coupled to the chassis and comprising two omnidirectional wheel systems each including an omnidirectional wheel, a battery housed in the chassis, the battery configured to supply power to drive each omnidirectional wheel and supply power to operate the one or more medical devices, a swivel column, a battery management system housed in the chassis, where the battery management system is configured to facilitate wired and/or wireless charging of the battery, a hybrid UIF handle with multi-directional sensing, a drive controller configured to automatically control the two omnidirectional wheel systems, wherein the battery is positioned between the forward and rearward wheel sets and rearward of the swivel column, the drive controller further configured to receive input from the hybrid UIF handle and control operation of the two omnidirectional wheel systems in response thereto, and a rear suspension system including a brace and a single centrally positioned coil spring, wherein each of the two omnidirectional wheel systems has a motor drive housed under the suspension brace and a wheel motor that drives the corresponding omnidirectional wheel via a split-drive axle. In a first example of the mobile platform, it includes a first and second force-sensing handle regions positioned to engage each hand of a user, wherein the controller includes instructions to receive inputs from the first force-sensing handle region and second force-sensing handle region and control operation of the two omnidirectional wheel systems in response thereto.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the most appropriate mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A mobile platform, comprising:
 a chassis configured to house one or more medical devices;

an omnidirectional wheel system including an omnidirectional wheel coupled to the chassis;

a battery housed in the chassis, the battery configured to supply power to drive the omnidirectional wheel system and/or supply power to operate the one or more medical devices; and a battery management system housed in the chassis, where the battery management system is configured to facilitate wired and/or wireless charging of the battery.

2. The mobile platform of claim 1, wherein the omnidirectional wheel system is a first omnidirectional wheel system of at least two omnidirectional wheel systems, and wherein the chassis includes a drive controller configured to automatically control the at least two omnidirectional wheel systems.

3. The mobile platform of claim 2, wherein the drive controller is configured to automatically control the at least two omnidirectional wheel systems to move the mobile platform to a charging station.

4. The mobile platform of claim 1, further comprising a controller configured to receive inputs from a user and control operation of the omnidirectional wheel system in response thereto.

5. The mobile platform of claim 4, wherein the controller includes instructions stored in memory executable to determine a stability parameter of a current configuration of the mobile platform and limit output of the omnidirectional wheel system in response to the determined stability parameter.

6. The mobile platform of claim 1, further comprising a swivel column.

7. The mobile platform of claim 6, wherein the mobile platform includes a forward wheel set and a rearward wheel set and the omnidirectional wheel system is part of the forward wheel set or the rearward wheel set, and wherein the battery is positioned between forward and rearward wheel sets, and rearward of the swivel column.

8. The mobile platform of claim 7, further comprising a rear suspension system including a brace and a single centrally positioned coil spring.

9. The mobile platform of claim 8, wherein the omnidirectional wheel system includes a motor drive housed under the suspension brace and a wheel motor that drives the omnidirectional wheel via a split-drive axle.

10. The mobile platform of claim 1, further comprising a handle with first and second force-sensing regions positioned along the handle to engage each hand of a user.

11. The mobile platform of claim 10, further comprising a controller configured to receive inputs from the user's hands through one or more of the force-sensing regions on the handle and control operation of the omnidirectional wheel system in response thereto.

12. The mobile platform of claim 11, wherein rotation of the omnidirectional wheel in the omnidirectional wheel system and an angle of drive torque of the omnidirectional wheel are both responsive to sensed force from the first and second force-sensing regions of the handle.

13. A method of operation of a mobile platform driven by an omnidirectional wheel system having a chassis configured to house one or more medical devices, comprising:

moving the mobile platform by driving one or more omnidirectional wheels with an electric motor and a battery responsive to a user input physically interfacing with the mobile platform;

wirelessly charging the battery; and controlling the moving of the mobile platform based on a configuration of a medical device coupled to the mobile platform.

14. The method of claim 13, where the controlling of motion includes limiting motion based on a determined stability parameter of the mobile platform.

15. The method of claim 14, where the controlling of motion includes limiting motion based on a center of gravity of the mobile platform and the medical device in combination.

16. The method of claim 14, wherein the moving of the mobile platform is in response to sensed forces from the handle, the moving including driving the omnidirectional wheels to move both longitudinally and laterally simultaneously.

17. The method of claim 16, wherein the medical device includes an arm, wherein controlling motion includes limiting a speed of the mobile device platform in a specified direction based on an arm position.

18. A mobile platform, comprising:

a chassis configured to house one or more medical devices;

a forward wheel set coupled to the chassis;

a rearward wheel set coupled to the chassis and comprising two omnidirectional wheel systems each including an omnidirectional wheel;

a battery housed in the chassis, the battery configured to supply power to drive each omnidirectional wheel and supply power to operate the one or more medical devices;

a swivel column;

a battery management system housed in the chassis, where the battery management system is configured to facilitate wired and/or wireless charging of the battery;

a hybrid user interface (UIF) handle with multi-directional sensing;

a drive controller configured to automatically control the two omnidirectional wheel systems, wherein the battery is positioned between the forward and rearward wheel sets and rearward of the swivel column, the drive controller further configured to receive input from the hybrid UIF handle and control operation of the two omnidirectional wheel systems in response thereto; and a rear suspension system including a brace and a single centrally positioned coil spring, wherein each of the two omnidirectional wheel systems has a motor drive housed under the suspension brace and a wheel motor that drives the corresponding omnidirectional wheel via a split-drive axle.

19. The mobile platform of claim 18, wherein the handle includes a first force-sensing handle region and a second force-sensing handle region positioned to engage each hand of a user, wherein the controller includes instructions to receive inputs from the first force-sensing handle region and the second force-sensing handle region and control operation of the omnidirectional wheel systems in response thereto.

* * * * *